United States Patent [19]
Fox et al.

[11] Patent Number: 6,001,882
[45] Date of Patent: Dec. 14, 1999

[54] PHOTOACTIVATED HYPERICIN AND THE USE THEREOF

[75] Inventors: Floyd Eliot Fox, Bellmawr, N.J.; Alain H. Rook, Wynnewood; Alfonso J. Tobia, Doylestown, both of Pa.

[73] Assignee: The Trustees of the University of Pennsylvania, Philadelphia, Pa.

[21] Appl. No.: 08/887,546

[22] Filed: Jul. 3, 1997

[51] Int. Cl.$^6$ .................................................. A61K 31/12
[52] U.S. Cl. ........................ 514/680; 514/863; 514/885; 514/903; 514/908
[58] Field of Search .................. 514/680, 863, 514/885, 903, 908

[56] References Cited

U.S. PATENT DOCUMENTS

| | | | |
|---|---|---|---|
| 4,898,891 | 2/1990 | Lavie et al. | 514/732 |
| 5,120,412 | 6/1992 | Mazur et al. | 204/151.87 |
| 5,316,768 | 5/1994 | Hughes et al. | 424/433 |
| 5,506,271 | 4/1996 | Meruelo et al. | 514/732 |
| 5,514,714 | 5/1996 | Meruelo et al. | 514/561 |

OTHER PUBLICATIONS

Agostinis et al., 1995, "Photosensitized Inhibition of Growth Factor–Regulated Protein Kinase by Hypericin", *Biochem. Pharmacol.* 49:1615–1622.
Anker et al., 1994, "Hypericin in adjuvant brain tumor therapy", *Drugs Future* 20:511–517.
Ault, 1983, Diag. Immunol. 1:2–10.
Boyum, 1964, "Separation of White Blood Cells", Nature 793–794.
Brockmann et al., 1953, "Die Synthese de Hypericins", Naturwiss. 40:411.
Brockmann et al., 1950, "Die Umwandung von Penicillopsin in Hypericin", Naturwiss. 38:47.
Calzavara–Pinton et al., 1996, "Photodynamic therapy with stemic administration of photosensitizers in dermatology", J. Photochem. Photobiol. B–Biol. 36:225–231.
Couldwell et al., 1994, "Hypericin: A Potential Antiglioma Therapy", *Neurosurg.* 35:705–710 [erratum appears in 1994, Neurosurgery 35:993.
Diwu et al., 1994, "Phototherapeutic Potential of Alternative Photosenitizers to Porphyrins",Pharmacol. Ther. 63:1–35.
Duran et al., 1986, "Hypericin and its Photodynamic Action", *Photochem. Photobiol.* 433:677–680.
Fox et al. 1993, "Evidence that TGF–β Can Inhibit Human T–Lymphocyte Proliferation through Paracrine and Autocrine Mechanisms", Cell. Immunol. 150:45–58.
Goodman et al., 1985, *The Pharmacological Basis of Therapeutics*, Macmillan, New York—too voluminous to submit.
Hamilton et al., 1996, "Inhibition of cellular growth and induction of apoptosis in pituitary adenoma cell lines by the protein kinase C inhibitor hypericin: potential therapeutic application", J. Neurosurg. 85:329–334.
Jarvis et al., 1994, Induction of Apoptotic DNA Fragmentation and Cell Death in HL–60 Human Promyelocytic Leukemia Cells by Pharmacological Inhibitors of Protein Kinase C$^1$, *Canc. Res.* 54:1707–1714.

Lavie et al., 1989, "Studies of the mechanisms of action of the antiretroviral agents hypericin and pseudohypericin", Proc. Natl. Acad. Sci. U.S.A. 86:5963–5967.
Lavie et al., 1995, "Hypericin as an inactivator of infectiour viruses in blood components", *Transfusion* 35:392–400.
Levy, 1994, "Photosensitizers in Photodynamic Therapy", Sem. Oncol. 21(6 Suppl. 15):4–10.
Longnecker, 1994, "Biochemical and Genetic Studies of Epstein–Barr Virus Latent Membrane Protein 2", Leukemia 8:546–550.
Neitzel, 1986, "A ruotine method for the establishment of permanent growoing lymphoblastoid cell lines", Hum. Gen. 73:320–326.
Parrish et al, 1974, "Photochemotherapy of Psoriasis and oral methoxypsoralen and long–wave ultraviolet light", *N. Engl. J. Med.* 291:1207–1211.
Polack, 1996, "c–myc activation renders proliferation of Epstein–Barr virus (EBV)–transformed cells independent of EBV nuclear antigen 2 and latent membrane protein 1", Proc. Natl. Acad. Sci. U.S.A. 93:10411–10416.
Ross et al., 1985, "Evaluation of an Automated Hematology System (Technicon H–1)", Arch. Pathol. Lab. Med. 110:803–808.
Sgonc, 1994, Simultnaeous determination of cell surface antigens and apoptosis:, Trends Gen. 10:41–42.
Song et al., 1979, J. Photochem. Photobiol. 29:1177–1197.
Wolff, 1997, "Should PUVA be abandoned?",New Eng. J. Med. 336:1090–1091.
Stringer et al., 1996, "The Accumulation of Protoporphyrin IX in Plaque Psoriasis After Topical Application of 5–Aminovulinic Acid Indicates a Potential for Superficial Photodyamic Therapy", J. Invest. Dermatol. 107:76–81.
Thomas et al., 1992, "Oxygen Dependence of Hypericin–Induced Phototoxicity to EMT6 Mouse Mammary Carcinoma Cells", *Photochem. Photobiol.* 55(6):831–837.
VIMRx Pharmaceuticals Inc., "Hypericin (VIMRxyn®), A Promising New Antiviral and Anticancer Agent", pp. 1–4 (1996).
Vandenbogaerde et al., 1996, "Antitumour Activity of Photosensitized Hypericin on A431 Cell Xenografts",*Anticanc. Res.* 16:1619–1626.
Zhang et al., 1996, "Malignant Glioma Sensitivity to Radiotherapy, High–dose Tamoxifen, and Hypericin: Corroborating Clinical Response in vitro: Case Report", Neurosurg. 38:587–591.
Zhang et al., 1995, "Growth inhibition and apoptosis in human neuroblastoma SK–N–SH cells induced by hypericin, a potent inhibitor of protein kinase C", *Canc. Lett.* 96:31–35.

*Primary Examiner*—Kimberly Jordan
*Attorney, Agent, or Firm*—Akin, Gump, Strauss, Hauer & Feld, L.L.P.

[57] ABSTRACT

The invention provides methods of using photoactivated hypericin compounds which, when photoactivated using visible or UV-A light, are useful for treating numerous diseases and disorders in mammals. The compounds of the invention are useful for inhibiting the proliferation and accumulation of mammalian leukocytes and for inducing apoptosis in mammalian leukocytes.

30 Claims, 13 Drawing Sheets

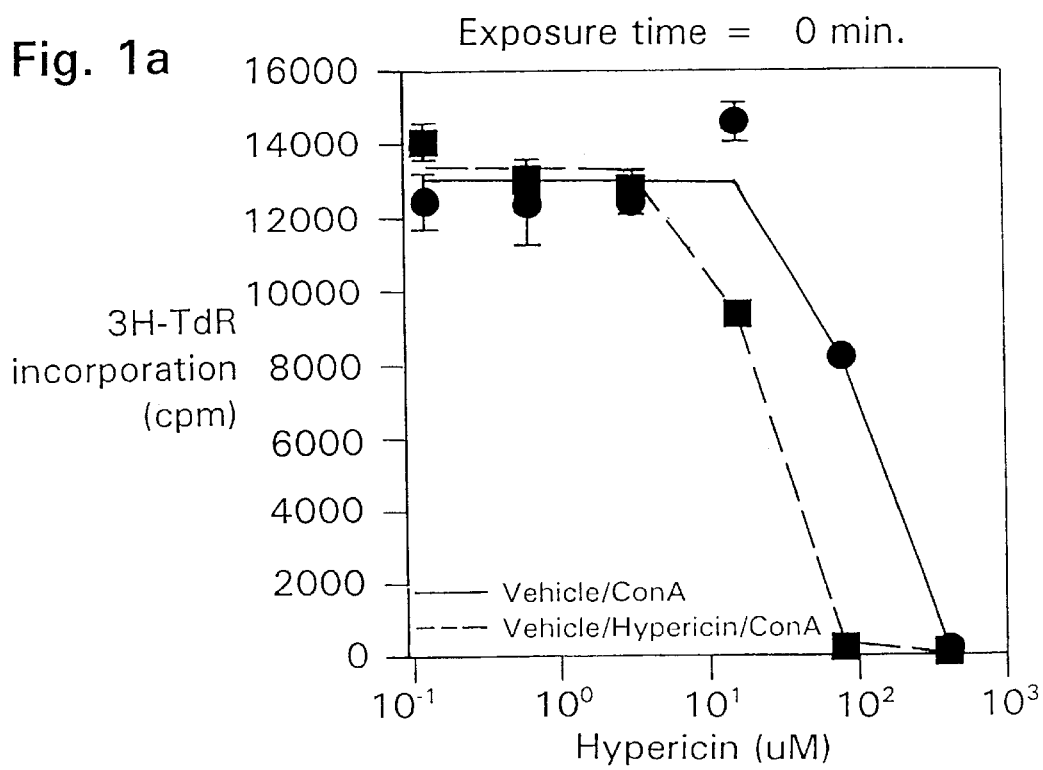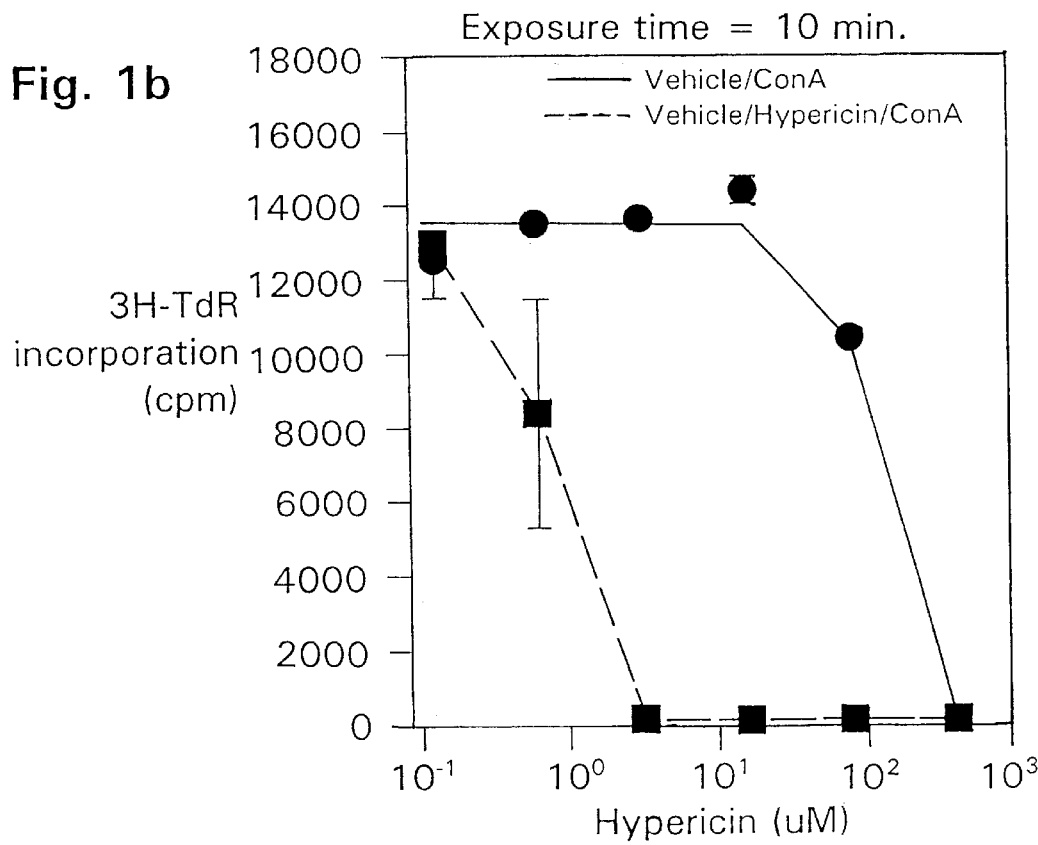

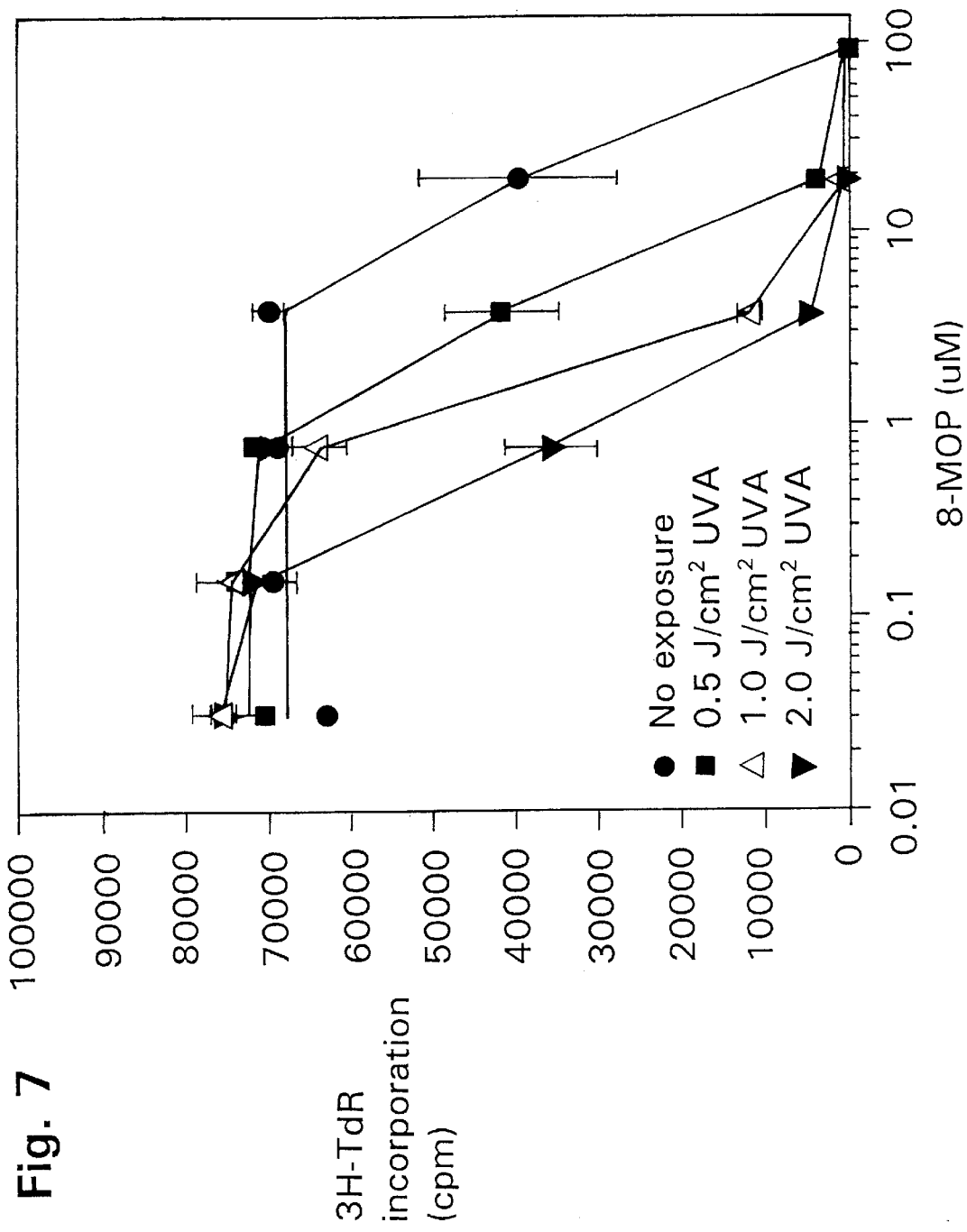

Fig. 8A
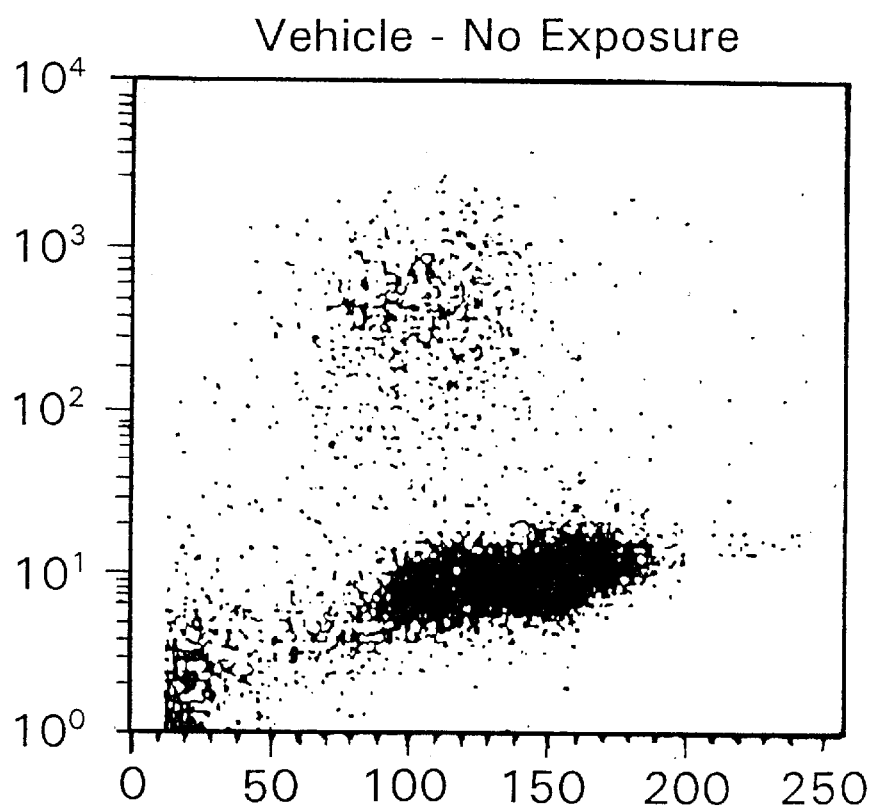
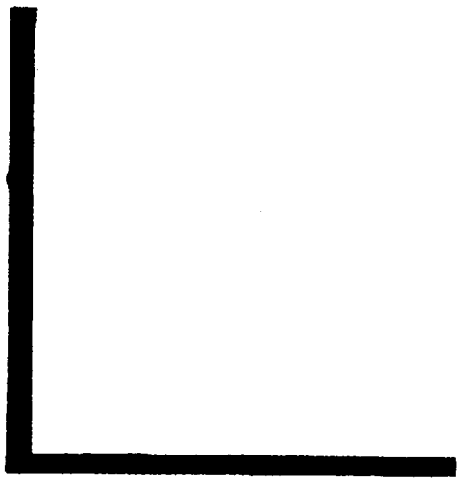

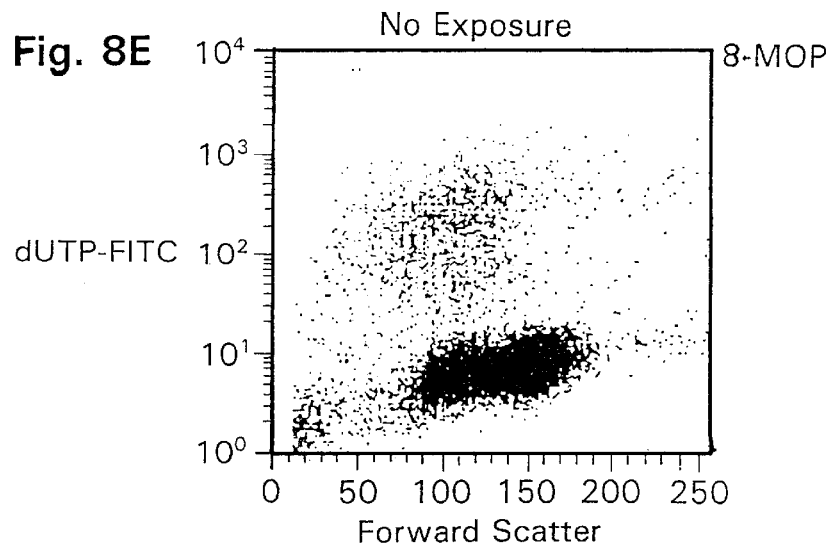
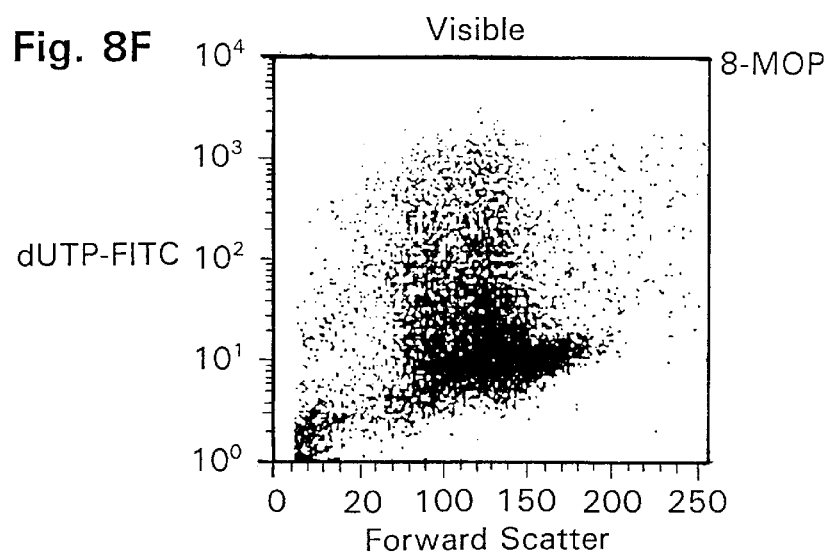
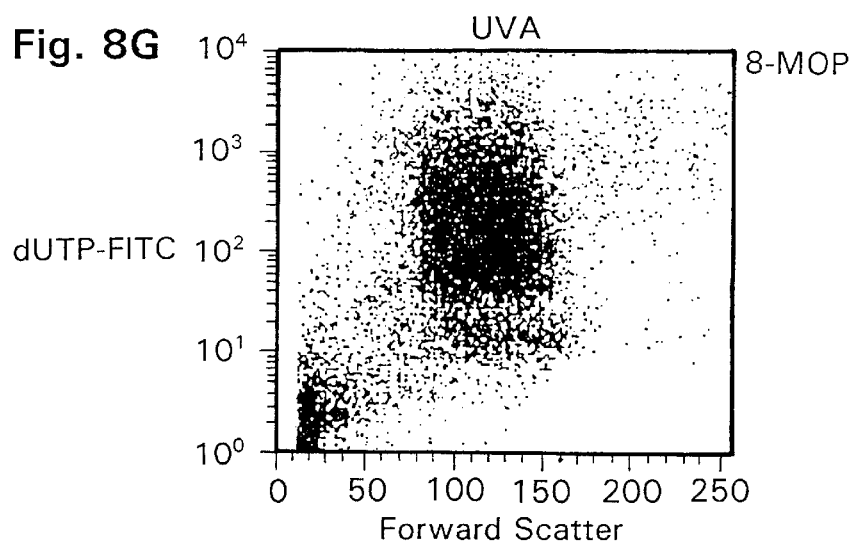

PHOTOACTIVATED HYPERICIN AND THE USE THEREOF

FIELD OF THE INVENTION

The field of the invention is inhibition of normal and pathological cell growth, proliferation, and accumulation.

BACKGROUND OF THE INVENTION

Recently, increasing attention has been devoted to photodynamic therapy (PDT) because of the discovery that many photosensitizer compounds, either naturally occurring or synthesized, exhibit remarkable anti-cancer and antiviral activities (Diwu et al., 1994, Pharmacol. Ther. 63:1–35).

Several studies have shown that benign hyperproliferative and hypervascular conditions such as psoriasis can be improved by photosensitization with porphyrins (Levy, 1994, Sem. Oncol. 21(6 Suppl. 15):4–10). Selective sensitization of psoriatic tissue using porphyrins has been demonstrated as an effective treatment for psoriasis and the efficacy of the treatment method may be related to the increased vascularity of psoriatic plaques (Stringer et al., 1996, J. Invest. Dermatol. 107:76–81). Another report using systemic tin-protoporphyrin in combination with long wavelength ultraviolet light suggests that this combination effects amelioration of psoriasis in psoriatic patients (Calzavara-Pinton et al., 1996, J. Photochem. Photobiol. B-Biol. 36:225–231).

One of the most commonly used regimens for the treatment of psoriasis, i.e. psoralen-ultraviolet A light (PUVA) treatment, is a form of PDT. PUVA treatment involves the administration to a patient of a psoralen compound, followed by illumination of the skin of the patient with light having a wavelength corresponding to ultraviolet A (UV-A) radiation. Although PUVA treatment provides relief from psoriasis, exposure of skin to UV-A radiation can have a number of undesirable effects, including a sunburn-like reaction and induction of skin tumors (Stern et al., 1997, New Eng. J. Med. 336:1090–1091).

Apart from the undesirable effects of UV radiation, psoralen, other furocoumarins such as 8-methoxypsoralen (8-MOP), and other types of photosensitizing agents such as hematoporphyrin derivatives, also have various disadvantages, including mutagenicity resulting from the ability of the compounds to intercalate into DNA, and toxicity of the compounds in patients.

Hypericin is a naturally occurring compound which is found in plants of the genus Hypericum, in insects of the genus Coccoidea, and in the ciliated protozoan *Stentor coeruleus*. Hypericin has been demonstrated to possess virucidal and antiviral activities (Lavie et al., 1989, Proc. Natl. Acad. Sci. U.S.A. 86:5963–5967; U.S. Pat. No. 4,898,891; U.S. Pat. No. 5,514,714; U.S. Pat. No. 5,506,271), and anti-tumor activities (Couldwell et al., 1994, Neurosurg. 35:705–710 [erratum appears in 1994, Neurosurgery 35:993]; Hamilton et al., 1996, J. Neurosurg. 85:329–334; Jarvis et al., 1994, Canc. Res. 54:1707–1714; Vandenbogaerde et al., 1996, Anticanc. Res. 16:1619–1625; Zhang et al., 1995, Canc. Lett. 96:31–35; Zhang et al., 1996, Neurosurg. 38:587–591).

Hypericin is maximally activated by visible light at wavelengths produced by a sodium lamp (590 nm) or cool white fluorescent light which significantly reduces the side effects associated with UV irradiation and permits deeper skin penetration. Hypericin has a relatively long half life (20–24 hours) which permits repeated light activation with single doses. This compound has been demonstrated in skin after systemic administration and it has been shown to be about 20% bioavailable following oral administration.

The photodynamic properties of hypericin have been described (Pace et al., 1941, J. Chem. Soc. 63:2570–2574)). Upon visible or UV light irradiation, hypericin in solution is capable of exciting oxygen to its singlet state and generating superoxide radicals, which can lead to oxidation of tryptophan imidazole groups in proteins, to oxidation of fatty acids in biological systems, or to other chemical reactions. Hypericin is maximally activated by light of about 570–650 nm wavelength, i.e. in the yellow region of the electromagnetic spectrum. Although hypericin has been known for many years, and although the application of non-photoactivated hypericin has been investigated in clinical studies of its anti-cancer and antiviral activities, very little is known about the mechanism of action of this compound at the biochemical or molecular level (Agostinis et al., 1995, Biochem. Pharmacol. 49:1615–1622). Photoreaction of hypericin has been demonstrated to produce singlet oxygen. In addition, there is evidence that hypericin inhibits protein kinase activity and thus, may exert its biological activity through pathways which are very different from, for example, psoralen (Song et al., 1979, J. Photochem. Photobiol. 29:1177–1197; Agostinis et al., 1995, Biochem. Pharmacol. 49:1615–1622). Furthermore, hypericin binds to phospholipids, such as cell membranes comprising phosphatidylcholine, and to retroviral particles, probably by associating with the lipid envelope thereof.

Photoactivation of hypericin prior to treatment therewith of an enveloped virus served to reduce the infectious titer of the enveloped virus, but did not inactivate the virus (Meruelo et al., U.S. Pat. No. 5,506,271). Exposure of hypericin to light has also been demonstrated to only slightly enhance hypericin's antiproliferative effects on glioma cells in vitro (Anker et al., 1994, Drugs Future 20:511–517). Hypericin has been reported to be incapable of inhibiting proliferation of leukemia cells (Jarvis et al., 1994, Canc. Res. 54:1707–1714). However, local illumination of the skin covering subcutaneously xenografted carcinoma cells in a nude mouse following intraperitoneal administration of hypericin to the mouse inhibited proliferation of these carcinoma cells (Vandenbogaerde et al., 1996, Anticanc. Res. 16:1619–1626). Lavie et al. (1995, Transfusion 35:392–400) demonstrated that photoactivated hypericin could be used to inactivate viruses in blood compositions in vitro, but reported no effect of hypericin on leukocytes. U.S. Pat. No. 5,514,714 (Meruelo et al.) discloses that administration of hypericin to a mammal can be effective to treat T-cell-mediated disorders. This reference did not investigate the use of photoactivated hypericin.

A long-felt need exists for photosensitizing agents which may be used to treat patients having a disorder, wherein the agent may be activated by non-UV light and wherein the combination of active agent and light is free of the deleterious side effects of known photosensitizing agents and UV light combinations.

SUMMARY OF THE INVENTION

The invention features a method of inhibiting proliferation of a leukocyte of a mammal, comprising administering to a population of mammalian leukocytes a composition which comprises an appropriate hypericin derivative and photoactivating the appropriate hypericin derivative, thereby effecting inhibition of proliferation of the leukocyte. In one aspect of the invention, proliferation of a leukocyte is characterized by accumulation of the leukocyte.

The invention also features a method of inducing apoptosis in a leukocyte of a mammal, comprising administering to a population of mammalian leukocytes a composition which comprises an appropriate hypericin derivative and photoactivating the appropriate hypericin derivative, thereby inducing apoptosis in the leukocyte. Preferably, the appropriate hypericin derivative is selected from the group which consists of hypericin, protohypericin, and pseudohypericin.

In one aspect of the invention, the step of photoactivating the appropriate hypericin derivative is continued until apoptosis has been induced in substantially all leukocytes in the mammal. Preferably, the mammal is a human. In yet another aspect, the human is a human in need of a bone marrow transplant. In another aspect, the human is afflicted with leukemia.

In another aspect of the invention, the step of photoactivating the appropriate hypericin derivative comprises providing illumination from a visible light source. Preferably, the visible light source emits light having a wavelength between about 500 nm and about 650 nm.

In another aspect of the invention, the step of photoactivating the appropriate hypericin derivative comprises providing illumination from a UV-A light source.

Preferably, in this aspect, the leukocyte is contained within a tissue of the mammal, and the composition further comprises a pharmaceutically acceptable carrier. In some aspects of the invention, the tissue is a dermatological tissue. According to one aspect of the invention, the step of photoactivating the appropriate hypericin derivative is performed after the step of administering the composition.

In another aspect of the invention, the step of administering the composition comprises orally administering the composition to the mammal. According to yet another aspect of the invention, the step of photoactivating the appropriate hypericin derivative comprises illuminating the dermatological tissue of the mammal.

In a further aspect, the step of administering the composition comprises topically administering the composition to the mammal. According to yet another aspect of the invention, the step of photoactivating the appropriate hypericin derivative comprises illuminating the dermatological tissue of the mammal.

In yet another aspect of the invention, the tissue of the mammal is a blood tissue. In one aspect, the step of photoactivating the appropriate hypericin derivative is performed after the step of administering the composition. In another aspect, the step of administering the composition comprises orally administering the composition to the mammal. In yet another aspect, the step of photoactivating the appropriate hypericin derivative comprises illuminating a dermatological tissue of the mammal.

In another aspect of the invention, the tissue of the mammal is a blood tissue and the step of photoactivating the appropriate hypericin derivative comprises extracorporeally illuminating the blood tissue of the mammal.

In a further aspect of the invention, the tissue of the mammal is a blood tissue and the step of administering the composition comprises topically administering the composition to the mammal. Preferably, the step of photoactivating the appropriate hypericin derivative comprises illuminating a dermatological tissue of the mammal. Also preferably, the step of photoactivating the appropriate hypericin derivative comprises extracorporeally illuminating the blood tissue of the mammal.

In yet another aspect of the invention, the leukocyte is contained within a tissue of the mammal, the composition further comprises a pharmaceutically acceptable carrier, and the mammal is afflicted with a hypericin-sensitive disease. Preferably, the hypericin-sensitive disease is selected from the group consisting of a leukocyte-associated disease, cutaneous T-cell lymphoma, myeloma, mastocytosis, an eosinophilic condition, transplant rejection, graft-versus-host disease, an EBV-mediated lymphoma, Burkitt's lymphoma, infectious mononucleosis, an EBV-associated B-cell lymphoma, an EBV-associated mesenchyal cutaneous tumor, a systemic immunologic process, an autoimmune disease, leukemia, lymphoma, psoriasis, a polymorphonuclear cell-related disease, Sweet's disease, pyoderma gangrenosum, and an allergic reaction.

In one embodiment, the mammal is a human, the hypericin-sensitive disease is psoriasis, the dermatological tissue of the human is a psoriatic tissue, and the step of illuminating the psoriatic tissue comprises exposing the psoriatic tissue to a visible light source.

In another embodiment, the mammal is a human, the hypericin-sensitive disease is cutaneous T-cell lymphoma, and the step of illuminating the dermatological tissue comprises exposing the dermatological tissue to a UV-A light source.

The invention also features a method of treating a mammal afflicted with a hypericin-sensitive disease, the method comprising the steps of administering to the mammal a composition comprising an appropriate hypericin derivative and an pharmaceutically-acceptable carrier and photoactivating the appropriate hypericin derivative.

In addition, the invention includes a method for predicting the in vivo response of a hypericin-sensitive-disease-affected tissue of a mammal to administration and photoactivation of an appropriate hypericin derivative, the method comprising the steps of obtaining a tissue sample from the hypericin-sensitive-disease-affected tissue, contacting the tissue sample with the appropriate hypericin derivative, photoactivating the appropriate hypericin derivative, and thereafter observing the response of the tissue sample, whereby the response of the tissue sample is predictive of the in vivo response of the hypericin-sensitive-disease-affected tissue of the mammal to administration and photo-activation of the appropriate hypericin derivative.

Data are presented as the mean±the standard deviation. Vertical bars, where visible, represent the standard deviation corresponding to the datum. Filled circles represent data obtained using cells which were exposed to the vehicle only, the concentration of vehicle being equal to the concentration of vehicle present in cultures to which the indicated concentrations of hypericin were administered. Filled squares represent data obtained using cells which were exposed to the vehicle and to hypericin. The cells corresponding to Panel A were not illuminated. The cells corresponding to Panel B were illuminated with visible fluorescent light for 20 minutes.

Figure 3:
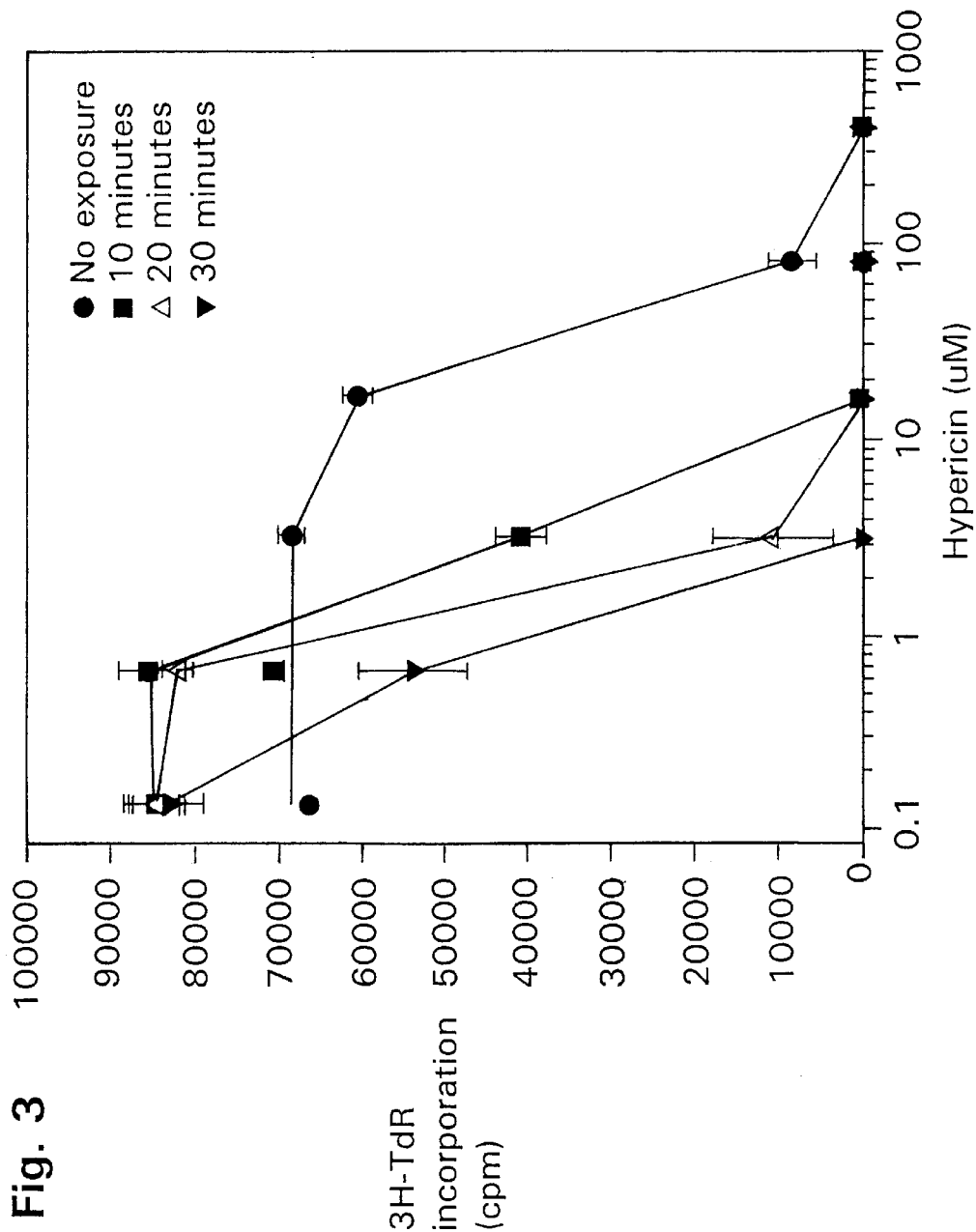

FIG. 3 is a graph which depicts the effect of hypericin on proliferation of EBV-transformed leukocytes. $^3$H-TdR incorporation was used as a measure of cell proliferation. Data are presented as the mean±the standard deviation. Vertical bars, where visible, represent the standard deviation corresponding to the datum. Filled circles represent data obtained using cells which were not illuminated. Filled squares represent data obtained using cells which were illuminated with visible fluorescent light for 10 minutes. Filled triangles represent data obtained using cells which were illuminated with visible fluorescent light for 20 minutes. Filled inverted triangles represent data obtained using cells which were illuminated with visible fluorescent light for 30 minutes.

Figure 4:
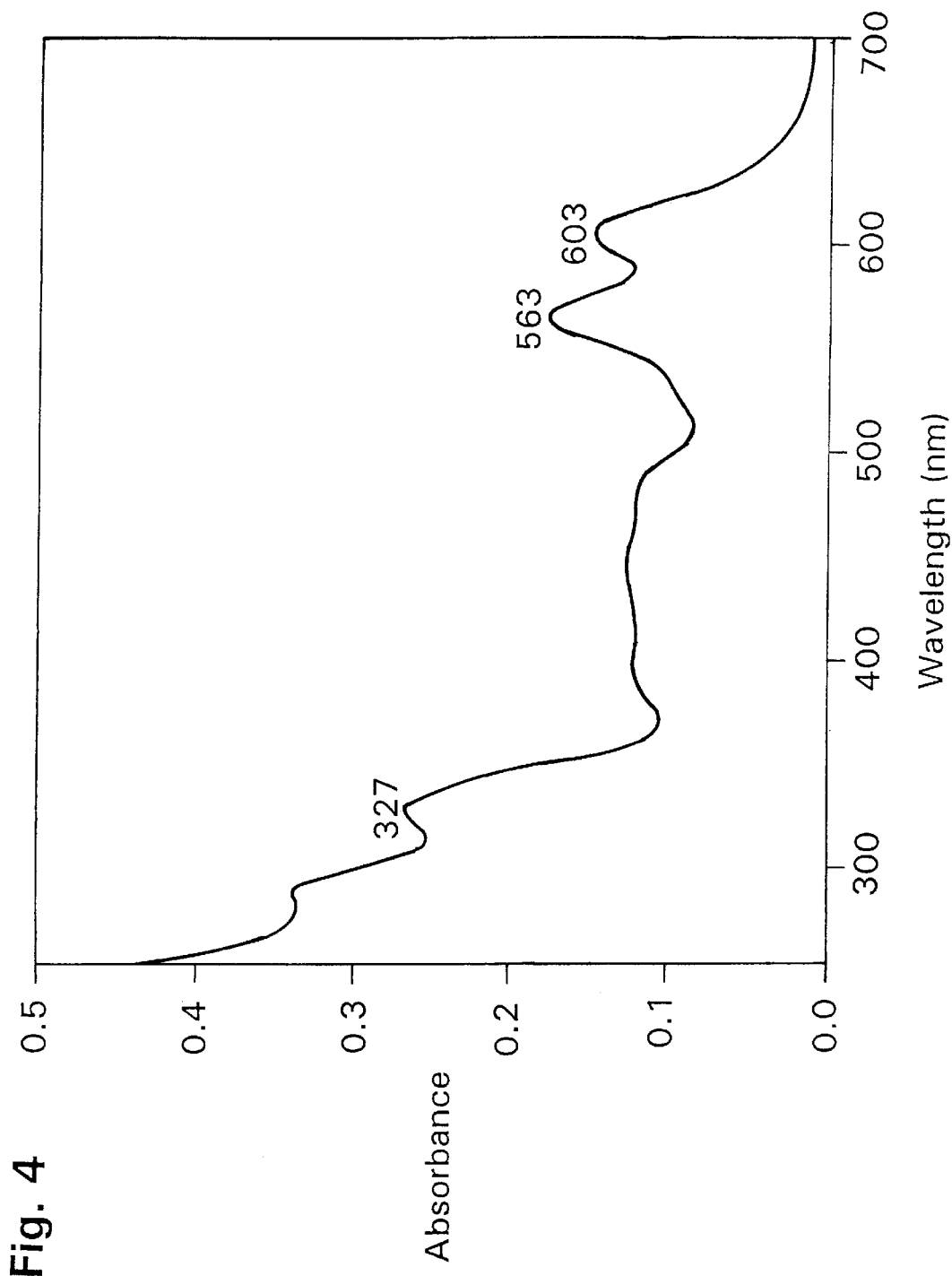

FIG. 4 is a graph which depicts the absorbance spectrum of a solution comprising 20 $\mu$M hypericin in phosphate-buffered saline. Absorbance maxima which were observed included maxima at 327 nm, 563 nm, and 603 nm.

Figure 5:
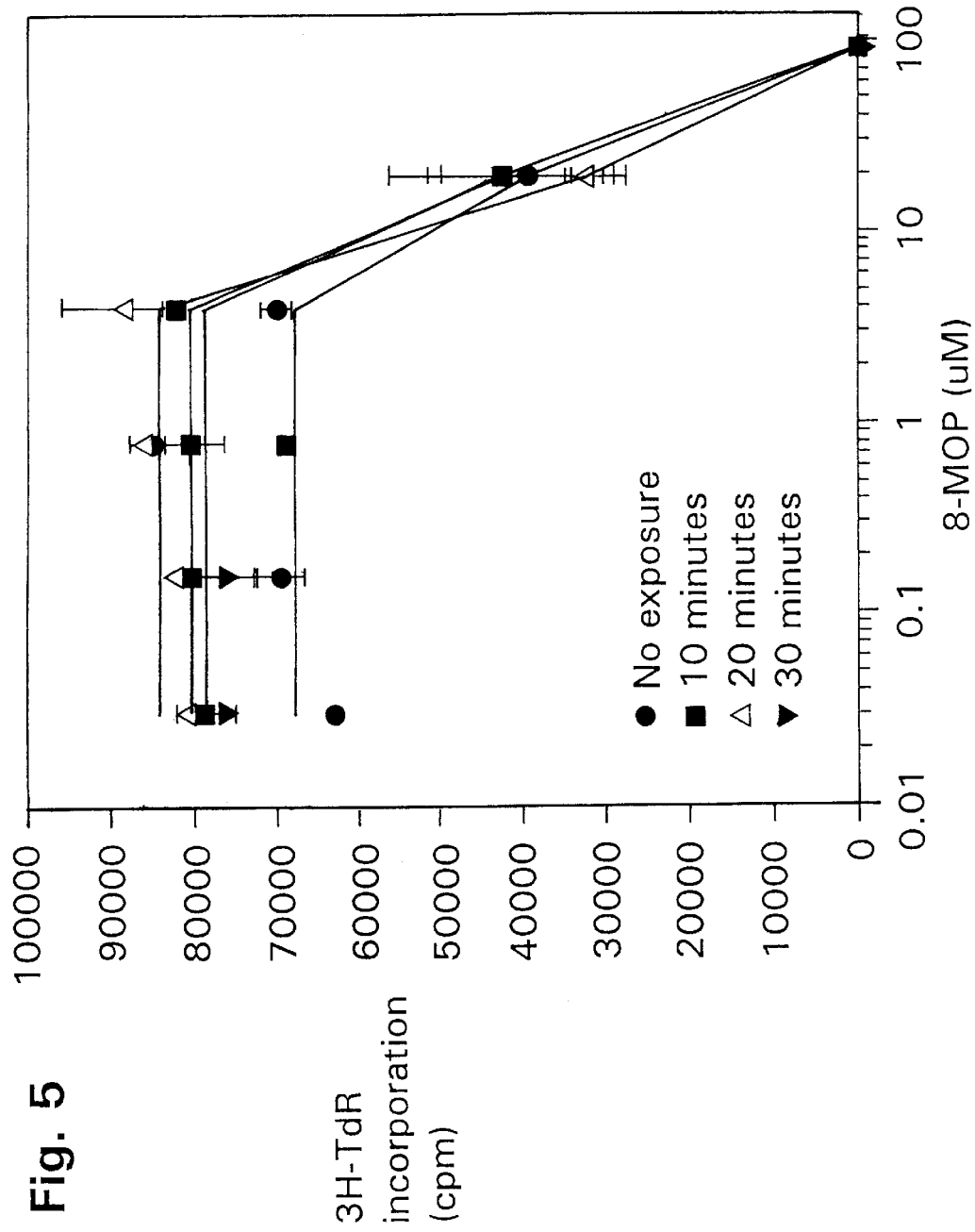

FIG. 5 is a graph which depicts the effect of 8-MOP on proliferation of EBV-transformed leukocytes. $^3$H-TdR incorporation was used as a measure of cell proliferation. Data are presented as the mean±the standard deviation. Vertical bars, where visible, represent the standard deviation corresponding to the datum. Filled circles represent data obtained using cells which were not illuminated. Filled squares represent data obtained using cells which were illuminated with visible fluorescent light for 10 minutes. Filled triangles represent data obtained using cells which were illuminated with visible fluorescent light for 20 minutes. Filled inverted triangles represent data obtained using cells which were illuminated with visible fluorescent light for 30 minutes.

Figure 6:
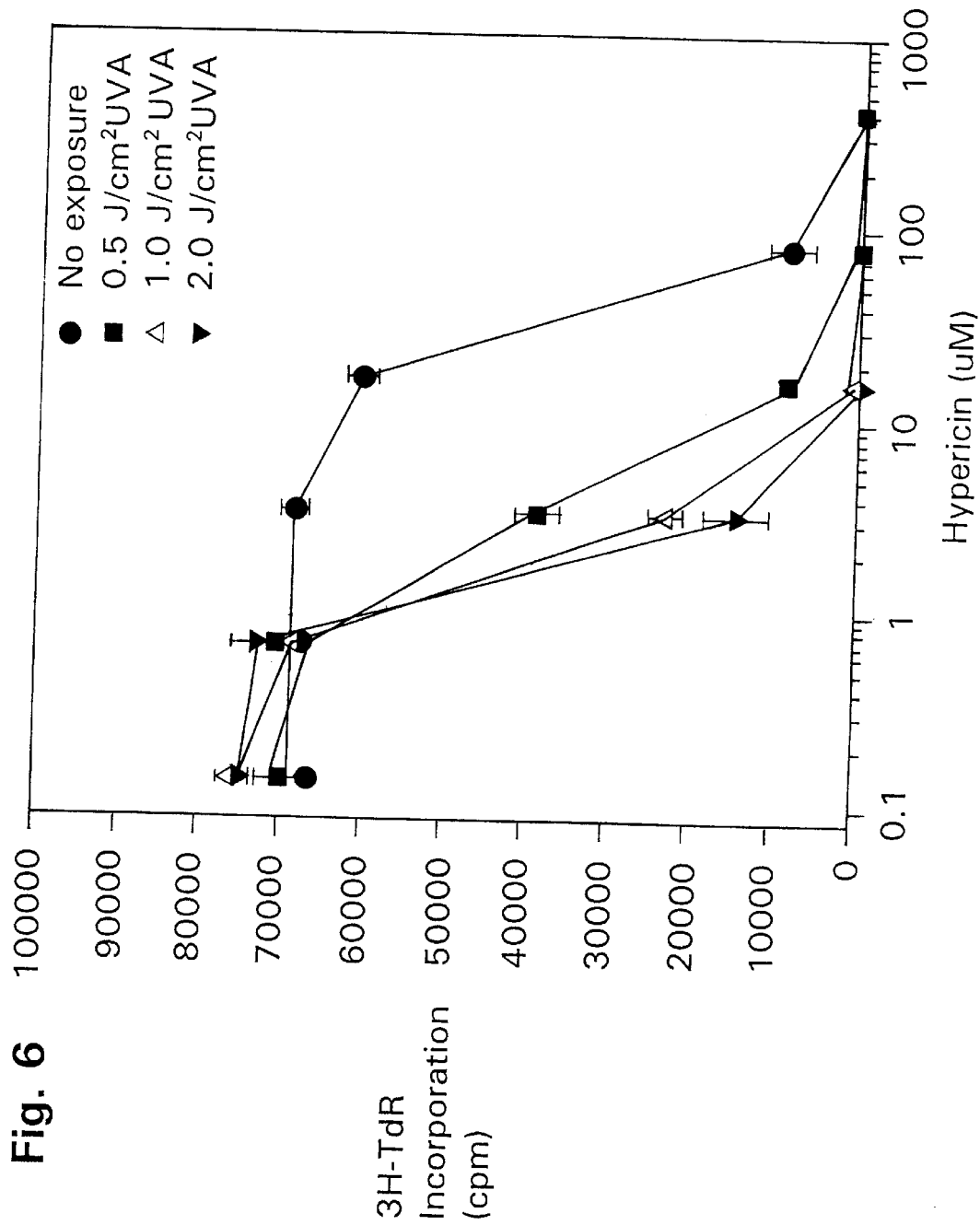

FIG. 6 is a graph which depicts the effect of hypericin on proliferation of EBV-transformed leukocytes. $^3$H-TdR incorporation was used as a measure of cell proliferation. Data are presented as the mean±the standard deviation. Vertical bars, where visible, represent the standard deviation corresponding to the datum. Filled circles represent data obtained using cells which were not illuminated. Filled squares represent data obtained using cells which were illuminated with 0.5 J/cm$^2$ UV-A light. Filled triangles represent data obtained using cells which were illuminated with 1.0 J/cm$^2$ UV-A light. Filled inverted triangles represent data obtained using cells which were illuminated with 2.0 J/cm$^2$ UV-A light.

FIG. 7 is a graph which depicts the effect of 8-MOP on proliferation of EBV-transformed leukocytes. $^3$H-TdR incorporation was used as a measure of cell proliferation. Data are presented as the mean±the standard deviation. Vertical bars, where visible, represent the standard deviation corresponding to the datum. Filled circles represent data obtained using cells which were not illuminated. Filled squares represent data obtained using cells which were illuminated with 0.5 J/cm$^2$ UV-A light. Filled triangles represent data obtained using cells which were illuminated with 1.0 J/cm$^2$ UV-A light. Filled inverted triangles represent data obtained using cells which were illuminated with 2.0 J/cm$^2$ UV-A light.

Figure 8B:
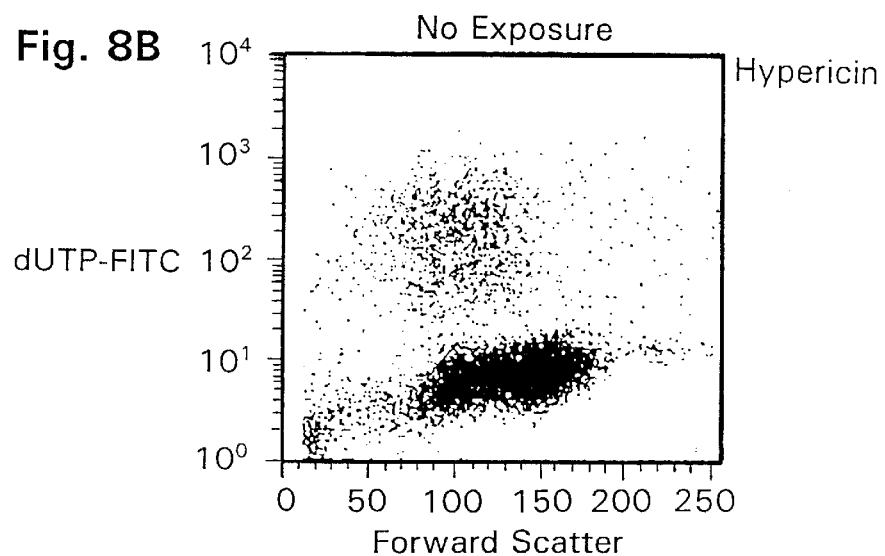
Figure 8C:
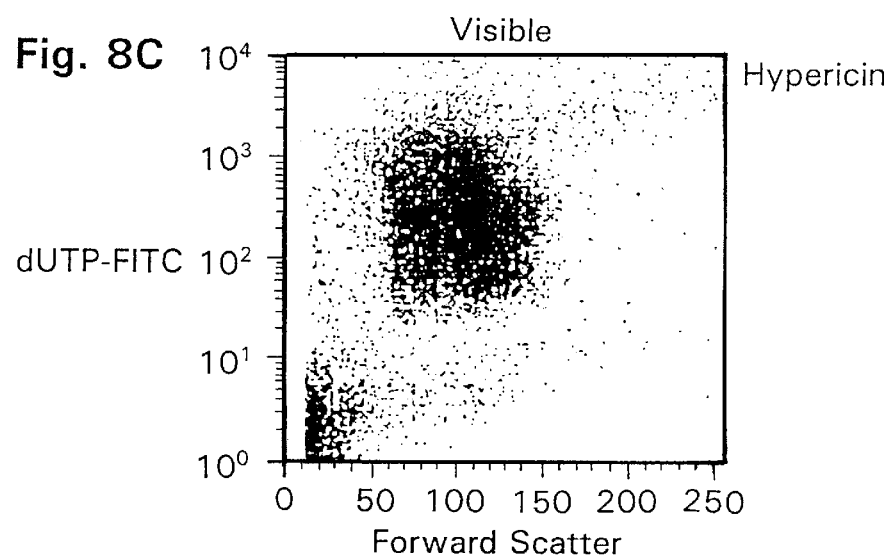
Figure 8D:
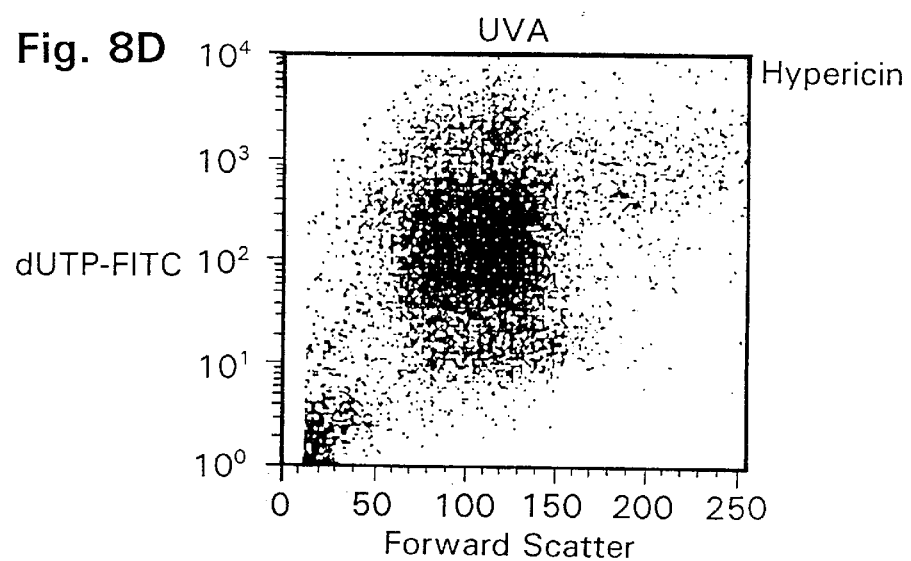

FIG. 8, comprising Panels A–G, is a series of graphs which represent distributions of cell types within various cultures, as assessed by flow cytometric cell sorting, using incorporation of dUTP-FITC into fragmented DNA as a selection criterion. Malignant leukocytes which have not been induced to undergo apoptosis are represented as points which are located below an imaginary horizontal line located at approximately $2\times10^1$ on the vertical axis of each graph. Malignant leukocytes which have been induced to undergo apoptosis are represented as points which are located above an imaginary horizontal line located at approximately $3\times10^1$ on the vertical axis of each graph. The graph in Panel A corresponds to cells which were not treated with either hypericin or 8-MOP and which were not illuminated. The graph in Panel B corresponds to cells which were treated with hypericin and which were not illuminated. The graph in Panel C corresponds to cells which were treated with hypericin and which were illuminated using visible light. The graph in Panel D corresponds to cells which were treated with hypericin and which were illuminated using UV-A light. The graph in Panel E corresponds to cells which were treated with 8-MOP and which were not illuminated. The graph in Panel F corresponds to cells which were treated with 8-MOP and which were illuminated using visible light. The graph in Panel G corresponds to cells which were treated with 8-MOP and which were illuminated using UV-A light.

Figure 9:
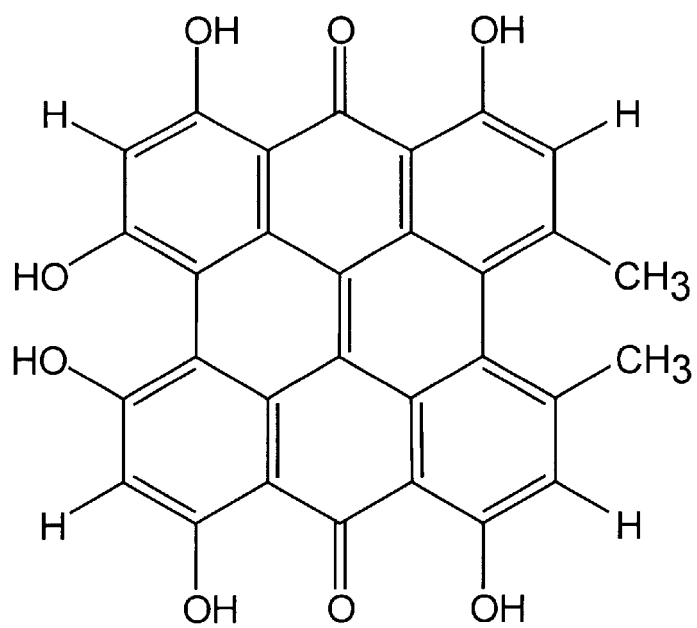

FIG. 9 is a representation of the chemical structure of hypericin.

Figure 10:
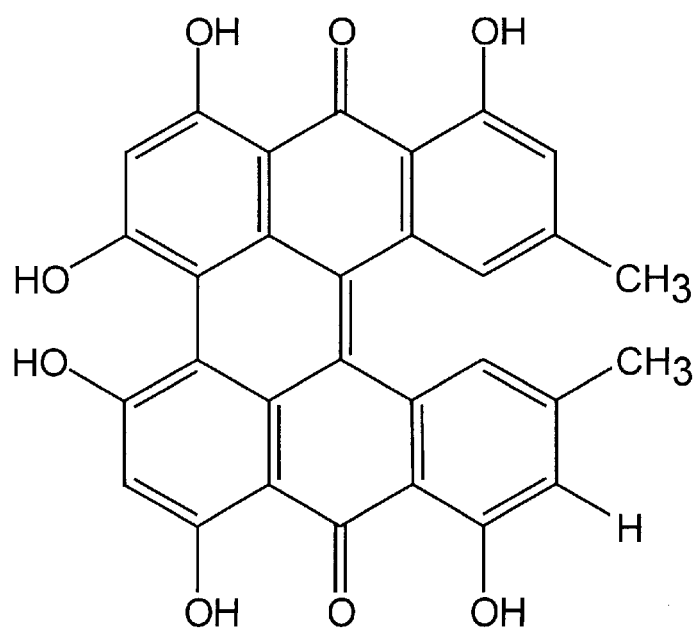

FIG. 10 is a representation of the chemical structure of protohypericin.

Figure 11:
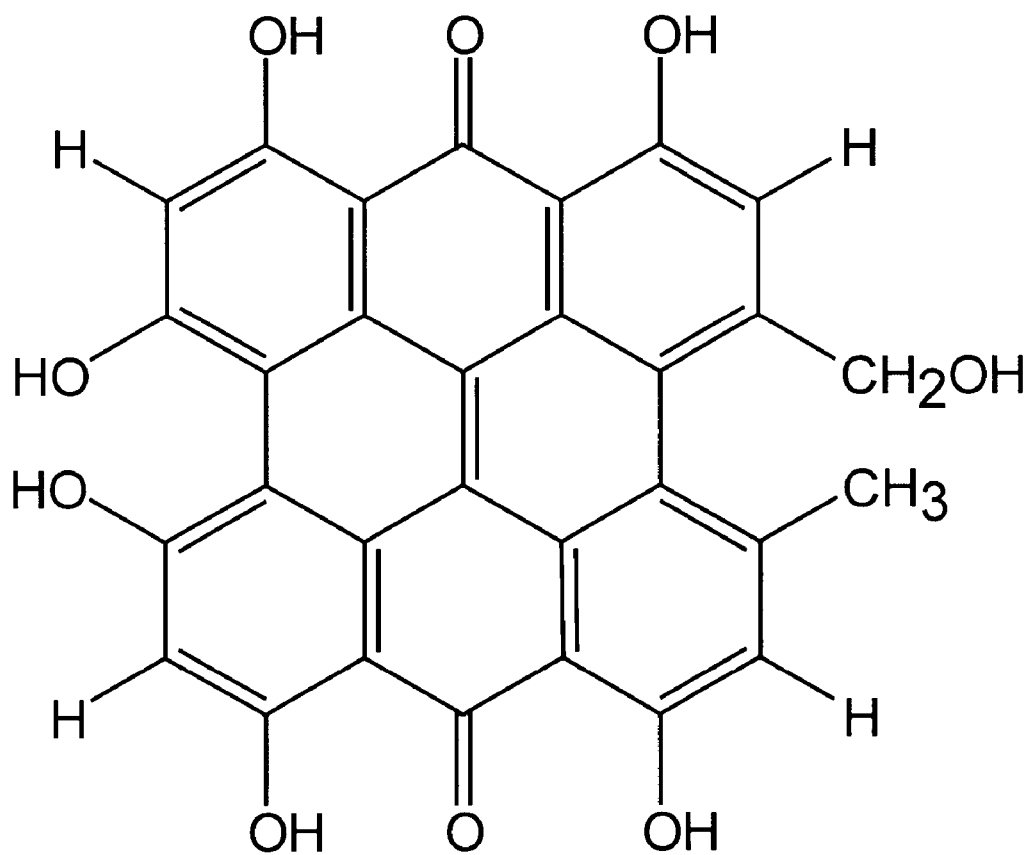

FIG. 11 is a representation of the chemical structure of pseudohypericin.

DETAILED DESCRIPTION

The invention features the use photoactivated hypericin and related compounds to treat a leukocyte-associated disease or disorder in a mammal including, but not limited to, diseases and disorders associated with normal leukocytes and those associated with abnormal leukocytes. The present invention includes the surprising discovery that visible- or UV-photoactivation of hypericin, decreases, relative to non-photoactivated hypericin, the concentration of hypericin required to inhibit leukocyte proliferation or accumulation, to induce apoptosis of leukocytes, or both. In preferred embodiments the decrease in the required concentration of hypericin is by a factor of about ten or more; more preferably, the decrease is by a factor of one hundred or more. This substantial increase in potency provides a significant clinical advantage for treatment of diseases such as cutaneous T-cell lymphoma (CTCL), psoriasis, and other diseases or disorders related to cell growth, proliferation, and accumulation, in that only small amounts of hypericin are required for treatment thereby reducing the potential for toxicity of this compound in the mammal being treated.

Preferably, the disease or disorder to be treated is a dermatological disease or disorder or a systemic immunologic disease or process. Also, preferably, photoactivation of hypericin is effected by illuminating the skin or the blood of the mammal using visible light comprising light having a wavelength between about 570 nm and about 650 nm.

For the treatment diseases or disorders which are caused by or characterized by the presence of malignant leukocytes in cutaneous tissue, a wavelength corresponding to UV-A light or to visible light is used in order to induce apoptosis of malignant leukocytes.

The methods of the invention, therefore, are particularly advantageous, in that photoactivation of hypericin permits the use of a lower concentration of hypericin in a mammal than would be required in the absence of photoactivation. Also, because hypericin does not share the numerous disadvantageous properties of other photosensitizing agents, such as mutagenicity resulting from the ability to intercalate into DNA, and toxicity, the use of hypericin in PDT is preferable to the use of other photosensitizing agents, particularly at the therapeutically effective hypericin concentrations which are disclosed herein. Furthermore, because hypericin can be activated using light having a wavelength in the visible spectrum, some of the disadvantages which accompany PDT using UV light may be avoided, such as a sunburn-like reaction and induction of skin tumors.

Some examples of diseases which may be treated according to the methods of the invention are discussed herein. The invention should not be construed as being limited solely to these examples, as other leukocyte-associated diseases which are at present unknown, once known, may also be treatable using the methods of the invention.

Treatment of Leukocyte-Associated Diseases in Mammals

The invention features the use photoactivated hypericin and appropriate hypericin derivatives to inhibit cell growth, proliferation, or accumulation of leukocytes, to induce apoptosis of leukocytes, or both, the leukocytes including, but not being limited to, neoplastic leukocytes, such as those associated with CTCL, transformed leukocytes, such as those associated with Epstein-Barr virus (EBV) infection, and non-neoplastic activated leukocytes, such as those associated with psoriasis and activated leukocytes associated with transplantation rejection.

Methods of administering hypericin to mammals have been described, its pharmacokinetics are understood, and its absorption by, distribution among, and metabolism in mammalian tissues has been reported (*Investigator's Drug Brochure,* VimRx Pharmaceuticals, Inc., Stamford, Conn., Apr. 27, 1995). Following administration to mammals, hypericin remains in the blood plasma, and may therefore affect leukocytes (*Investigator's Drug Brochure,* supra). Vandenbogaerde et al. (1996, Anticanc. Res. 16:1619–1626) demonstrated that local illumination of mammalian skin permitted sufficient light to pass through the skin to photoactivate hypericin for the treatment of solid xenografted tumors. The results of Vandenbogaerde et al. therefore demonstrate that sufficient light penetrates mammalian dermatological tissues to photoactivate hypericin in blood plasma within blood and lymph vessels within mammalian dermatological tissues. Photopheresis of mammalian blood may also be used to photoactivate hypericin therein.

As described in the experimental examples presented herein, photoactivated hypericin is capable of inhibiting proliferation or accumulation of or of inducing apoptosis of normal, malignant, and transformed leukocytes. Therefore, administration of an appropriate hypericin derivative to mammalian blood and photoactivation of the appropriate hypericin derivative may be used to treat any leukocyte-associated disease. Preferably, the mammal to be treated is a human.

Psoriasis

A treatment for psoriasis is now exemplified. It is to be understood that this example is not limited to psoriasis, but may be analogously used to treat any leukocyte-associated disease in which leukocytes exhibit abnormal proliferation or accumulation or exhibit abnormal reactivity which contributes to the severity of a lesion in a dermatological tissue.

To treat psoriasis in a human, the human is given an appropriate hypericin derivative in a pharmaceutically acceptable carrier. Preferably, the appropriate hypericin derivative is hypericin, although protohypericin or pseudohypericin may also be used. In one embodiment, the appropriate hypericin derivative is administered topically to the psoriatic tissue of the human, and the psoriatic tissue is thereafter illuminated. Preferably, a visible light source is used to illuminate the psoriatic tissue, although a UV-A light source may also be used.

In another embodiment, the appropriate hypericin derivative is given orally, and the psoriatic tissue is thereafter illuminated. When this method is performed, it is advantageous to delay illumination of the psoriatic tissue for a period of minutes or hours following administration of the appropriate hypericin derivative, in order to permit the appropriate hypericin derivative to become bioavailable in the psoriatic tissue.

In another embodiment, the appropriate hypericin derivative is administered both topically and either orally or subcutaneously. Using this method, more complete distribution of the appropriate hypericin derivative in the psoriatic tissue may be achieved prior to illumination of the psoriatic tissue.

Cutaneous T-Cell Lymphoma

A treatment for CTCL is now exemplified. It is to be understood that this example is not limited to CTCL, but may be analogously used to treat any leukocyte-associated disease in which leukocytes exhibit abnormal proliferation or accumulation or exhibit abnormal reactivity and are present in dermatological tissue.

To treat CTCL in a human, the human is given an appropriate hypericin derivative in a pharmaceutically acceptable carrier. Preferably, the appropriate hypericin derivative is hypericin, although protohypericin or pseudohypericin may also be used. In one embodiment, the appropriate hypericin derivative is administered systemically. In another embodiment, the appropriate hypericin derivative is administered orally. In still another embodiment, the appropriate hypericin derivative is administered topically.

Following administration of the appropriate hypericin derivative, the appropriate hypericin derivative is photoactivated. Visible or UV-A light can be used to photoactivate the appropriate hypericin derivative, as described herein. In a preferred embodiment, the skin of the human is illuminated. In another embodiment, standard photopheresis techniques are used to illuminate the blood of the human.

Leukemia

A treatment for leukemia is now exemplified. It is to be understood that this example is not limited to leukemia, but may be analogously used to treat any leukocyte-associated disease in which malignant leukocytes are present in circulating blood plasma.

To treat leukemia in a human, the human is given an appropriate hypericin derivative in a pharmaceutically acceptable carrier. Preferably, the appropriate hypericin derivative is hypericin, although protohypericin or pseudohypericin may also be used. In one embodiment, the appropriate hypericin derivative is administered systemically. In another embodiment, the appropriate hypericin derivative is administered orally. In still another embodiment, the appropriate hypericin derivative is administered topically.

Following administration of the appropriate hypericin derivative, the appropriate hypericin derivative is photoactivated. Visible or UV-A light can be used to photoactivate the appropriate hypericin derivative, as described herein. In a preferred embodiment, standard photopheresis techniques are used to illuminate the blood of the human. In another embodiment, the skin of the human is illuminated.

Inducing Apoptosis in Substantially All Leukocytes in a Mammal

A treatment which is useful to induce apoptosis in substantially all leukocytes in a mammal is now exemplified. The treatment is useful for subjects, particularly humans, afflicted with leukemia or in need of a bone marrow transplant. It is to be understood that this example is not limited to bone marrow transplantation and leukemia uses, but may be analogously used whenever it is desired to eliminate substantially all leukocytes from the mammal. The treatment for inducing apoptosis in substantially all leukocytes in a mammal may also be used to treat mammalian bone marrow from a donor mammal, prior to transplant, to reduce or eliminate a graft-versus-host reaction in the bone marrow recipient mammal.

By "substantially all leukocytes" is meant that the number of leukocytes which remain following treatment is insufficient to provoke an autologous immune response to a bone marrow transplant performed following treatment.

Numerous methods for enumerating leukocytes in a mammal are known in the art (Ault, 1983, Diag. Immunol. 1:2–10; Ross et al., 1985, Arch. Pathol. Lab. Med. 110:803–808), including direct microscopic observation of the blood or lymph of the mammal. Preferably, the method induces apoptosis in more than ninety percent of the lymphocytes of a mammal. More preferably, the method induces apoptosis in more than ninety-nine percent of the lymphocytes of a mammal. Still more preferably, the treatment induces apoptosis in all but a number of leukocytes of a mammal, which number is not detectable using known methods of enumerating leukocytes.

The human is given an appropriate hypericin derivative in a pharmaceutically acceptable carrier. Preferably, the appropriate hypericin derivative is hypericin, although protohypericin or pseudohypericin may also be used. In one embodiment, the appropriate hypericin derivative is administered systemically. In another embodiment, the appropriate hypericin derivative is administered orally. In still another embodiment, the appropriate hypericin derivative is administered topically.

Following administration of the appropriate hypericin derivative, the appropriate hypericin derivative is photoactivated. In one embodiment, visible light is used to photoactivate the appropriate hypericin derivative. In another embodiment, UV-A light is used to photoactivate the appropriate hypericin derivative. In one embodiment, standard photopheresis techniques are used to illuminate the blood of the human. In another embodiment, the skin of the human is illuminated. Illumination continues until apoptosis has been induced in substantially all leukocytes. In one embodiment, additional administrations of the appropriate hypericin derivative are made, in order to maintain the in vivo concentration of the appropriate hypericin derivative at an effective concentration.

The methods of the invention are useful for inhibiting the proliferation or accumulation of leukocytes, inducing apoptosis in leukocytes, or both, both in vivo and in vitro. When used in vivo, the methods comprise administering an appropriate hypericin derivative to a mammal and photoactivating the hypericin, preferably following administration. When used in vitro, the methods comprise administering an appropriate hypericin derivative to a population of leukocytes and photoactivating the hypericin. The population of leukocytes may be obtained from a single mammal or from a plurality of mammals and pooled. The population of leukocytes may be returned to the mammal from which it was obtained following treatment of the population using the methods of the invention. Furthermore, the population may be subjected to cell-sorting procedures, using a flow cytometer, for example, either before or after treatment using the methods of the invention.

No reference or combination of references suggests that photoactivated hypericin is particularly useful for the treatment of leukocyte-associated diseases. Furthermore, no reference or combination of references suggests that photoactivation of hypericin in one tissue of the body of a subject is effective to treat a hypericin-sensitive disorder in a different tissue of the body.

Definitions

As used herein, the term "appropriate hypericin derivative" means hypericin, protohypericin, pseudohypericin, or a combination thereof. It is clear to one of skill in the art that numerous insignificant modifications may be made to the chemical structure of hypericin, protohypericin, or pseudohypericin, and that many such modifications will not significantly alter the biological activity of the molecule. Hence, hypericin, protohypericin, and pseudohypericin molecules which have been insignificantly modified, such that the biological activity is not significantly altered, are included within the definition of an appropriate hypericin derivative. One of skill in the art will appreciate that they may use the methods taught herein to distinguish modified hypericin, protohypericin, or pseudohypericin molecules having insignificantly altered biological activity from those having significantly altered biological activity.

As used herein, the term "hypericin" means the chemical compound alternatively identified as hypericin, as VIMRxyn (®, VimRx Pharmaceuticals, Inc., Wilmington, Del.), as 1,3,4,6,8,13-Hexahydroxy-10,11,dimethyl-phenanthro[1,10,9,8,-opqra]perylene-7,14-dione, as 4,5,7,4',5',7'-hexahydroxy-2,2'-dimethylnaphtho-dianthrone, and as hypericum red. Methods for preparing or isolating hypericin have been described (U.S. Pat. No. 5,120,412; Brockmann et al., 1942, Ann. 553: 1; Brockmann et al., 1953, Naturwiss. 40:411; Brockmann et al., 1951, Naturwiss. 38:47). Hypericin has the chemical structure shown in FIG. 9.

As used herein, the term "protohypericin" means the chemical compound having the chemical structure shown in FIG. 10. Protohypericin may be made using, for example, the methods taught in U.S. Pat. No. 5,120,412. It has been demonstrated that protohypericin is converted to hypericin upon exposure to visible light (U.S. Pat. No. 5,120,412).

As used herein, the term "pseudohypericin" means the chemical having the chemical structure shown in FIG. 11. Methods for making pseudohypericin are described in U.S. Pat. No. 4,898,891.

As used herein, the terms "leukocyte", "lymphocyte", "lymphoid cell", and "peripheral blood mononuclear cell" each mean a cell derived from a hematopoietic cell which is not an erythrocyte or a thrombocyte. These terms are used interchangeably herein to denote a cell which is derived from a hematopoietic cell and which is affected by photoactivated hypericin as described herein.

As used herein, the leukocyte against which photoactivated hypericin is to be effective is contained within a culture medium wherein treatment may be effected ex vivo. Alternately, the leukocyte is contained within a tissue of a mammal, or is contained within a cell separation medium, where, again, treatment may be effected ex vivo. One of skill in the art will appreciate that the methods of the invention are useful for inhibiting proliferation or accumulation of a leukocyte, inducing apoptosis in a leukocyte, or both, in a variety of leukocyte environments.

As used herein, the term "transformed leukocyte" means a leukocyte which has been contacted with an agent which causes the leukocyte to exhibit abnormal proliferation or accumulation including, but not limited to, a virus, whereby when the agent is removed, the leukocyte continues to exhibit abnormal proliferation or accumulation.

As used herein, the terms "malignant leukocyte" and "neoplastic leukocyte" are synonymous and mean a leukocyte in which a normal mechanism for controlling proliferation of the leukocyte has been disabled, whereby the leukocyte exhibits abnormal proliferation and accumulation or cell death mechanisms.

As used herein, the term "psoriatic tissue" means a tissue which exhibits a lesion or an abnormality associated with psoriasis.

As used herein, the term "leukemic tissue" means a tissue including, but not limited to blood, bone marrow, and lymph, which comprises a neoplastic lymphocyte.

As used herein, the term "lymphoma" means a tissue including, but not limited to blood, bone marrow, and lymph, which comprises a neoplastic non-phagocytic leukocyte.

As used herein, the term "photoactivation" and grammatical forms thereof refer to a process by which, upon absorption of a quantum of energy corresponding to a photon of light having a given wavelength, a chemical compound is enabled to participate in or undergo a chemical reaction at a reaction rate which is greater than the corresponding reaction rate in the absence of photoactivation.

As used herein, the term "hypericin-sensitive disease" means a disease or disorder of a mammal which is either caused by or characterized by cells which exhibit abnormal proliferation or accumulation in or abnormal reactivity within at least one tissue of the mammal, wherein hypericin is capable of inhibiting proliferation or accumulation of the cells, of inducing apoptosis of the cells, or both. Hypericin-sensitive disease include, but are not limited to, leukocyte-associated diseases, cutaneous T-cell lymphomas, myelomas, mastocytosis, eosinophilic conditions, transplant rejections, graft-versus-host diseases, EBV-mediated lymphomas, Burkitt's lymphoma, infectious mononucleosis, EBV-associated B-cell lymphomas, EBV-associated mesenchymal cutaneous tumors, systemic immunologic processes, autoimmune diseases, leukemias, lymphomas, psoriasis, polymorphonuclear cell-related diseases, Sweet's disease, pyoderma gangrenosum, and allergic reactions.

As used herein, the term "cells which exhibit abnormal proliferation or accumulation in a tissue" means cells in a subject having a disease or disorder in which cells proliferate or accumulate to a greater degree than the corresponding cells in a healthy individual. As used herein, it is immaterial whether the disease or disorder results from the abnormal proliferation or accumulation of the cells or the abnormal cell proliferation or accumulation is merely a symptom of the disease or disorder. It is understood that accumulation of leukocytes represents the net result of proliferation of the leukocyte population in a subject and apoptosis of leukocytes in the subject.

As used herein, the term "cells which exhibit abnormal reactivity with at least one tissue" means cells in a subject having a disease or disorder, which cells, when contacted with a tissue in the subject, cause the tissue to exhibit a characteristic associated with the disease or disorder.

As used herein, the term "leukocyte-associated disease" means a hypericin-sensitive disease wherein the cells are leukocytes. Specific examples of leukocyte-associated diseases include, but are not limited to, psoriasis, CTCL, lymphoma, leukemia, acute lymphocytic leukemia, multiple sclerosis, myasthenia gravis, scleroderma, polymyositis, autoimmune disease, graft-versus-host disease, graft rejection, Graves disease, Addison's disease, autoimmune uveoretinitis, autoimmune thyroiditis, pemphigus vulgaris, systemic lupus erythematosus, and rheumatoid arthritis. Leukocyte-associated diseases may be identified using the method for predicting the in vivo response of a tissue as described herein, wherein the tissue is a tissue comprising leukocytes.

As used herein, the term "hypericin-sensitive-disease-affected tissue" means a tissue in which the cells which cause a hypericin-sensitive disease or by which a hypericin-sensitive disease is characterized, exhibit abnormal proliferation or accumulation or exhibit abnormal reactivity.

As used herein, the term "response of a hypericin-sensitive-disease-affected tissue" means the alleviation or non-alleviation of the abnormal behavior of the cells which cause a hypericin-sensitive disease or by which a hypericin-sensitive disease is characterized.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

As used herein, the term "$IC_{50}$" means the concentration of hypericin required to effect 50% inhibition of the biological phenomenon being measured.

As used herein, the term "dermatological tissue" means any of the tissues comprising mammalian skin, including, but not limited to, epidermis, dermis, and hypodermis.

As used herein, the term "blood tissue" means any of the tissues comprising mammalian blood, including, but not limited to, whole blood, lymph, and populations of cells separated from whole blood using methods known in the art.

As used herein, the term "tissue sample" means at least one cell obtained from a tissue.

As used herein, the term "visible light source" means a device, a body, a chemical reaction, or any other source from which emanates electromagnetic radiation having a wavelength between about 430 nm and about 690 nm. Specific examples of visible light sources include, but are not limited to, fluorescent white lights, sodium lamps, and the sun. It is preferred that the wavelength of the visible light be between about 500 nm and about 650 nm.

As used herein, the term "UV-A light source" means a device, a body, a chemical reaction, or any other source from which emanates electromagnetic radiation having a wavelength between about 200 and about 430 nm. Specific examples of UV-A light sources include, but are not limited to, UV lamps and the sun.

As used herein, the term "UV-A light" means electromagnetic radiation having a wavelength between about 320 nm and about 400 nm.

As used herein, the verb "to illuminate" means to direct light onto the object of the verb.

As used herein the phrase "to extracorporeally illuminate a blood tissue" means to direct light onto a blood tissue which has been withdrawn from a subject. The phrase specifically includes, but is not limited to, directing light onto a blood tissue which has been withdrawn from a subject and which is to be reintroduced into the subject following illumination. One of skill in the art is aware of numerous photopheresis techniques which may be used to extracorporeally illuminate a blood tissue.

The invention also encompasses the use of pharmaceutical compositions of an appropriate hypericin derivative to practice the methods of the invention, the compositions comprising an appropriate hypericin derivative and a pharmaceutically acceptable carrier.

As used herein, the term "pharmaceutically acceptable carrier" means a chemical composition with which an appropriate hypericin derivative may be combined and which, following the combination, can be used to administer the appropriate hypericin derivative to a mammal.

VIMRxyn (®, VimRx Pharmaceuticals, Inc., Wilmington, Del.) is an example of a pharmaceutical composition which comprises synthetic hypericin in a pharmaceutically-acceptable carrier for oral delivery to humans. VIMRxyn® is described in *Investigator's Drug Brochure* (1995, VimRx Pharmaceuticals, Inc., Wilmington, Del.).

The pharmaceutical compositions useful for practicing the invention may be administered to deliver a dose of between 10 ng/kg/day and 10 mg/kg/day. In one embodiment, the invention envisions administration of a dose which results in a concentration of hypericin between 10 nM and 80 $\mu$M in a hypericin-sensitive-disease-affected tissue of a mammal during illumination of a dermatological tissue or of a blood tissue of the mammal. The pharmaceutical compositions may be administered in single or multiple doses each day during therapy.

Pharmaceutical compositions that are useful in the methods of the invention may be administered systemically in oral solid dosage forms, ophthalmic, suppository, aerosol, topical or other similar dosage forms. Sustained-release formulations are also contemplated. In addition to the appropriate hypericin derivative, such pharmaceutical compositions may contain pharmaceutically-acceptable carriers and other ingredients known to enhance and facilitate drug administration. Other possible dosage forms, such as nanoparticles, liposomes, resealed erythrocytes, and immunologically based systems may also be used to administer an appropriate hypericin derivative according to the methods of the invention. Formulations of compounds for administration to humans are well known in the art and can be found, for example in *The Pharmacological Basis of Therapeutics* (Goodman et al., 1985, Macmillan, New York).

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLE 1

The Effect of Photoactivated Hypericin on Proliferation of Leukocytes

This example relates to data which establish that hypericin exerts a significantly enhanced antiproliferative effect on normal human lymphocytes when hypericin-treated lymphocytes are exposed to fluorescent visible light or to UV-A light. Photoactivated hypericin is about ten times more potent an inhibitor of cell proliferation than non-photoactivated hypericin when used to treat normal, malignant, or transformed lymphocytes.

The materials and methods used in this example are now described.

Lymphocytes and Cell Culture Techniques

The ability of hypericin to inhibit lymphocyte proliferation was tested using three different types of lymphocytes. In two of the types of lymphocytes, the mitogen, ConA, was used to induce proliferation, as described (Fox et al., 1993, Cell. Immunol. 150:45–58). The third type of lymphocytes used in this example proliferated actively in vitro without the need for mitogenic stimulation. The three types of lymphocytes which were used in this example were: PBMC obtained from a normal human subject and stimulated with ConA; PBMC, including malignant CD4+ T-lymphocytes, obtained from a human subject having CTCL and stimulated with ConA; and PBMC obtained from a normal human subject, which PBMC were exposed to Epstein-Barr virus (EBV) after being obtained from the subject, to produce transformed lymphocytes. It is known that EBV-transformed B-lymphocytes proliferate actively in vitro (Polack, 1996, Proc. Natl. Acad. Sci. U.S.A. 93:10411–10416; Longnecker, 1994, Leukemia 8:546–550).

The PBMC obtained from the human subject having CTCL comprised almost exclusively (>90%) CD4$^+$ T-cells and the vast majority of those CD4$^+$ cells expressed a single T-cell receptor variable beta chain clonotype, which indicated that they represented a single malignant clone.

Peripheral blood mononuclear cells (PBMC) were obtained by separating them from whole blood, using Ficoll-Paque separation techniques and media (Boyum, 1964, Nature 793–794). After they were obtained, PBMC were resuspended in RPMI 1640 medium, which comprised 10% (v/v) fetal bovine serum (GIBCO, Grand Island, N.Y.), and were distributed into the wells of 96-well microtiter plates. PBMC transformed using EBV were made as described (Neitzel, 1986, Hum. Gen. 73:320–326)

A stock solution comprising 2000 $\mu$M hypericin was prepared in 2% (v/v) benzyl alcohol (approximately 1 mg of hypericin per ml of solution). This stock solution stored at 4° C. in the dark. A stock solution comprising 462.5 $\mu$M 8-methoxypsoralen (8-MOP) was prepared in 2% (v/v) benzyl alcohol. 8-MOP was obtained from Sigma (St. Louis, Mo.).

Serial 5-fold dilutions of the hypericin stock solution and of the 8-MOP stock solution were made using the medium as the diluent, and 25 $\mu$l of one of the stock solutions, of a serial dilution thereof, or of the diluent was added to preselected wells of the microtiter plate. Hence, the final concentrations of hypericin which were used in the culture medium for normal leukocytes and for transformed leukocytes were 400 $\mu$M, 80 $\mu$M, 16 $\mu$M, 3.2 $\mu$M, 0.64 $\mu$M, and 0.13 $\mu$M, and the concentrations of hypericin which were used in the culture medium for malignant leukocytes were 400 $\mu$M, 80 $\mu$M, 16 $\mu$M, 3.2 $\mu$M, 0.64 $\mu$M, 0.13 $\mu$M, 0.026 $\mu$M, 0.0051 $\mu$M, 0.0010 $\mu$M, 0.20 nM, 0.041 nM, and 0.0082 nm. In cultures of transformed leukocytes in which 8-MOP was used, the concentrations of 8-MOP which were used were 92.5 $\mu$M, 18.5 $\mu$M, 3.7 $\mu$M, 0.74 $\mu$M, 0.15 $\mu$M, and 0.030 $\mu$M. Thereafter, ConA was then added to preselected wells to achieve a final concentration of 10 $\mu$g/ml of ConA in those wells. Wells containing appropriate control mixtures were also prepared, which did not contain hypericin or 8-MOP.

Microtiter culture plates were prepared in subdued fluorescent light, in order to keep uncontrolled photoactivation of hypericin to a minimum. Following preparation of the microtiter culture plates, preselected plates were illuminated with fluorescent visible light for 10–30 minutes, using four fluorescent bulbs (type F15T8CW, TFC Inc., Taiwan) spaced at a distance of 9 cm above the plates. Other preselected plates were illuminated with 0.5–2 Joules per square centimeter UV-A light using a UV-A light box containing 8 UVAR 06-91 bulbs. Still other preselected plates were not exposed to light. The covers of plates which were exposed to light were left in place during illumination.

Following illumination, plates which had been illuminated were placed into a dark incubator which was maintained at 37° C. Non-illuminated plates were placed into the incubator immediately after preparation. All plates were incubated for seventy-two hours. During the final eighteen hours of incubation, tritiated thymidine ($^3$H-TdR) was added to each well of each plate. No extraordinary precautions were used to prevent light exposure during the addition of $^3$H-TdR.

Lymphocyte Proliferation Assay

Lymphocyte proliferation was assessed by measuring the extent of incorporation of $^3$H-TdR into newly synthesized DNA within the cells at the end of the seventy-two hour incubation period, as described (Fox, 1993, Cell. Immunol. 150:45–58). The concentration of hypericin required to effect a 50% inhibition of leukocyte proliferation ($IC_{50}$) was determined using a logarithmic curve fitting algorithm.

The results of the experiments of this example are now described and are summarized in Table 1.

TABLE 1

Concentrations of hypericin or of 8-MOP which effect a 50% inhibition of ConA-induced cell proliferation ($IC_{50}$) of normal ("N"), neoplastic ("CTL"), or transformed ("EBV") PBMC. The values presented in the table represent the $IC_{50}$ ($\mu$M) observed for the indicated agent following the illumination conditions indicated. "J/sc" means Joules per square centimeter. "ND" means not determinable.

| | | | Light Source and Quantity | | | | | |
| --- | --- | --- | --- | --- | --- | --- | --- | --- |
| | | | Visible | | | UV-A | | |
| Agent | Cells | None | 10 min | 20 min | 30 min | 0.5 J/sc | 1 J/sc | 2 J/sc |
| Hypericin | N | 22 | 0.76 | 0.11 | 0.41 | | | 2.9 |
| | N | 23.2 | 0.68 | 0.18 | 0.17 | 4.6 | 2.1 | 0.7 |
| | CTL | 34 | | 0.34 | | | | |
| | CTL | 9.1 | 0.4 | ND | ND | 1.8 | 0.57 | ND |
| | CTL | 74.5 | | 0.53 | | | | |
| | EBV | 36 | 3.2 | 1.8 | 0.75 | 3.7 | 2.1 | 2.0 |
| 8-MOP | N | 33.5 | 33.5 | 33.5 | 33.5 | 0.96 | 0.17 | 0.15 |
| | CTL | 4.4 | 3.6 | 3.6 | 3.1 | 0.74 | 0.2 | ND |
| | EBV | 19.4 | 18.7 | 17.3 | 18.9 | 4.2 | 1.6 | 0.7 |

Normal Leukocytes

Figure 1C:
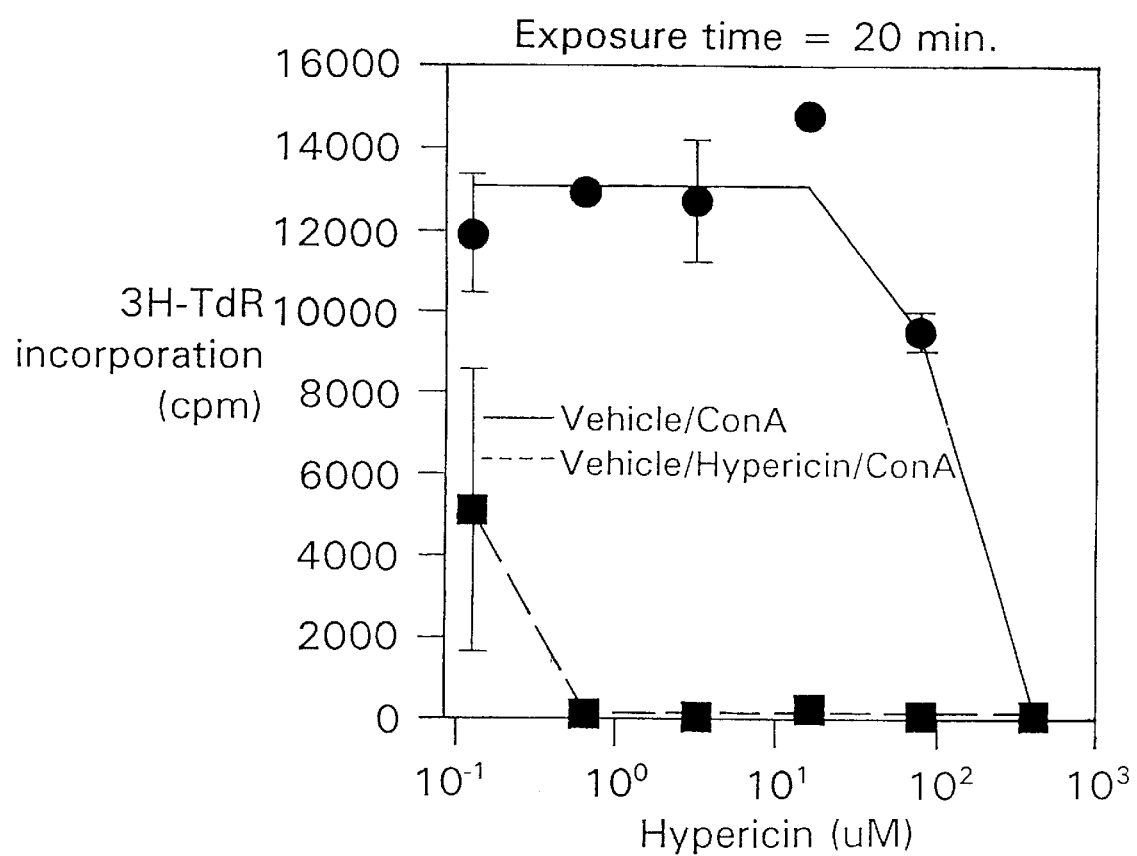
FIG. 1, comprising Panels A, B, and C, is a series of graphs, each of which depicts the effect of hypericin, or of the vehicle in which hypericin was dissolved, on proliferation of normal leukocytes, as induced by the mitogen ConA. $^3$H-TdR incorporation was used as a measure of cell proliferation. Data are presented as the mean±the standard deviation. Vertical bars, where visible, represent the standard deviation corresponding to the datum. Filled circles represent data obtained using cells which were exposed to the vehicle only, the concentration of vehicle being equal to the concentration of vehicle present in cultures to which the indicated concentrations of hypericin were administered. Filled squares represent data obtained using cells which were exposed to the vehicle and to hypericin. The cells corresponding to Panel A were not illuminated. The cells corresponding to Panels B and C were illuminated with visible fluorescent light for 10 and 20 minutes, respectively.

The results from studies involving normal leukocytes are depicted in FIG. 1. In cultures of normal lymphocytes which were illuminated for 10 minutes, the $IC_{50}$ for hypericin was 0.8 $\mu$M (FIG. 1, Panel B). Proliferation of normal lymphocytes was completely inhibited in culture medium comprising 3.2 $\mu$M hypericin when the medium was illuminated for 10 minutes. When the medium comprising normal lymphocytes was illuminated for 20 minutes, the $IC_{50}$ for hypericin was 0.1 $\mu$M, and complete inhibition of cell proliferation was observed at a concentration of 0.64 $\mu$M hypericin (FIG. 1, Panel C). The increased level of inhibition observed when hypericin-treated leukocytes were illuminated for 20 minutes, compared with illumination for 10 minutes, suggests that there is an optimal activation time needed for maximal efficacy of hypericin. Illumination of hypericin-treated lymphocytes for 30 minutes did not significantly increase inhibition of cell proliferation, which suggests that the optimal activation time is between 10 and 20 minutes.

When the medium comprising normal leukocytes was not illuminated, the $IC_{50}$ for hypericin was 22 $\mu$M (FIG. 1, Panel A). It should be noted that the culture medium comprised traces of benzyl alcohol used to prepare the hypericin stock solution. At the dilutions corresponding to the two highest concentrations of hypericin used in the culture medium, the benzyl alcohol in the medium inhibited the proliferation of leukocytes, as indicated by the solid lines in FIG. 1, Panels A, B, and C. For this reason, cultures not comprising hypericin exhibited cell proliferation inhibition which had an apparent the $IC_{50}$ of 86 $\mu$M. Because the $IC_{50}$ observed in cultures not comprising hypericin differed very little from the $IC_{50}$ observed in the cultures comprising hypericin which were not illuminated, it is apparent that the $IC_{50}$ for non-photoactivated hypericin is even greater than that reported herein. A more accurate estimate of the $IC_{50}$ value may be obtained by repeating this experiment completely in the dark using a hypericin stock solution which does not comprise an apparent cell proliferation inhibitor such as benzyl alcohol. The composition of such a stock solution are apparent to one of skill in the art.

Malignant Leukocytes

Figure 2A:
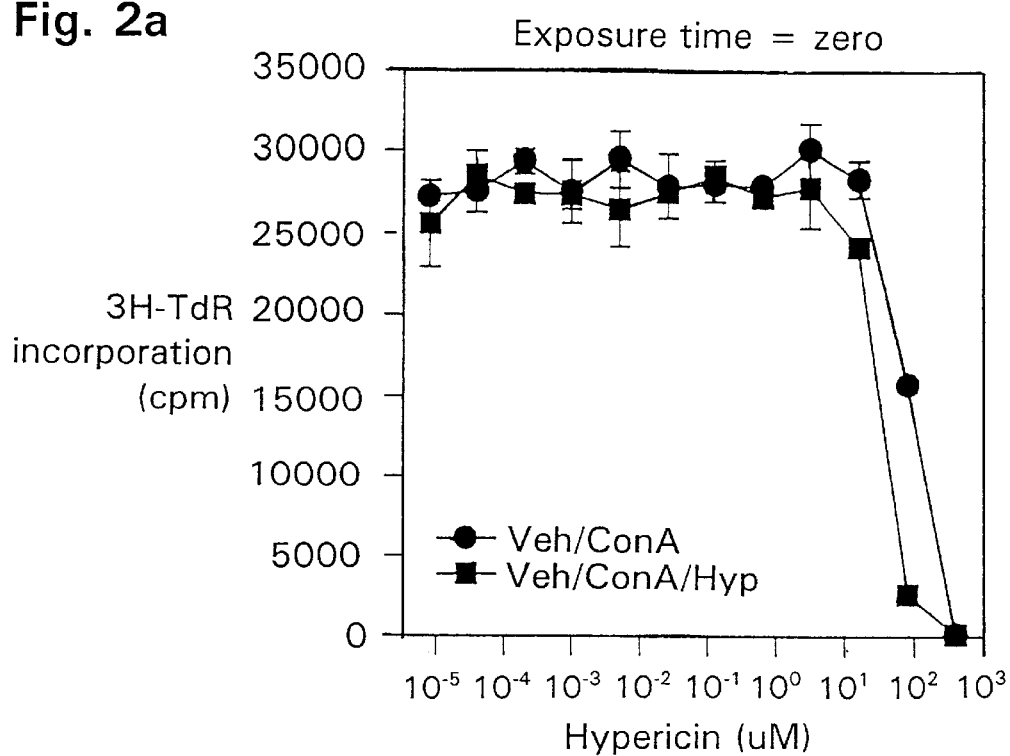
FIG. 2, comprising Panels A and B is a pair of graphs, each of which depicts the effect of hypericin or of the vehicle in which hypericin was dissolved on proliferation of malignant leukocytes, as induced by the mitogen ConA. $^3$H-TdR incorporation was used as a measure of cell proliferation.
Figure 2B:
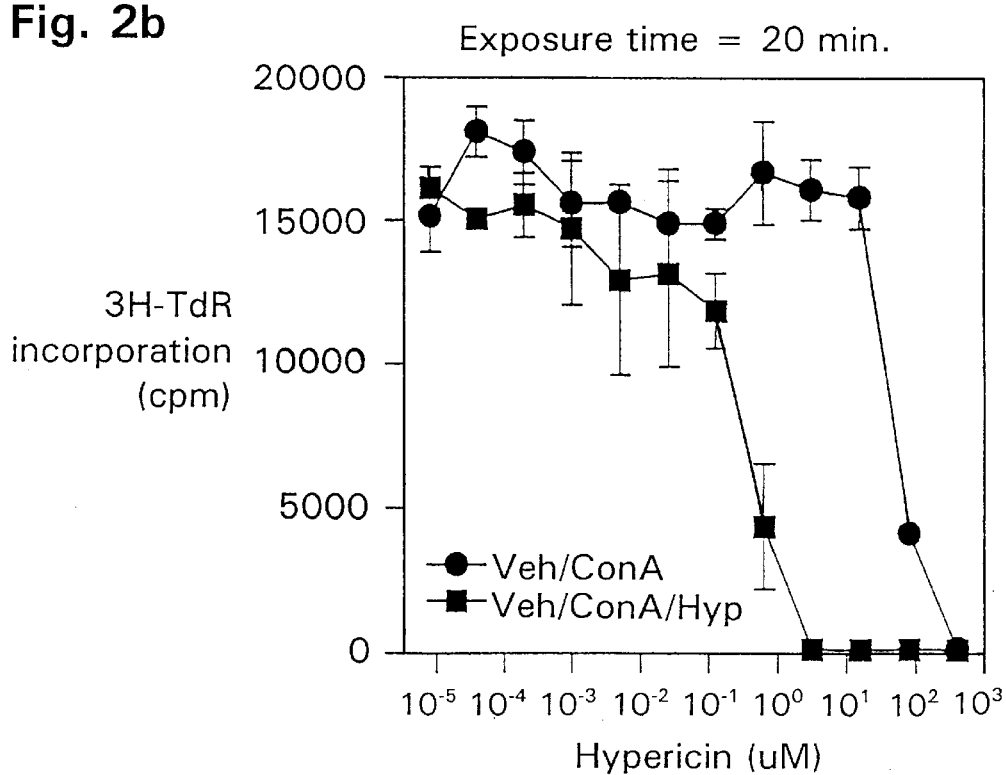

The results from studies involving malignant leukocytes obtained from a patient having CTCL are depicted in FIG. 2. In cultures of malignant leukocytes which were illuminated for 20 min, the $IC_{50}$ for hypericin was 0.3 $\mu$M, and complete inhibition of cell proliferation was observed at a concentration of 3.2 $\mu$M hypericin (FIG. 2, Panel B).

In cultures of malignant leukocytes which were not illuminated, the $IC_{50}$ for hypericin was 34 $\mu$M (FIG. 2, Panel A). At the dilutions corresponding to the two highest concentrations of hypericin used in the culture medium, the benzyl alcohol in the medium inhibited the proliferation of leukocytes, as indicated by the solid lines in FIG. 2, Panels A and B. For this reason, cultures not comprising hypericin exhibited cell proliferation inhibition which had an apparent the $IC_{50}$ of between 58 and 83 $\mu$M. As with the results obtained using normal leukocytes, because the $IC_{50}$ observed in cultures of malignant leukocytes that did not comprise hypericin differed very little from the $IC_{50}$ observed in the cultures of malignant leukocytes that comprised hypericin and were not illuminated, it is apparent that the $IC_{50}$ for non-photoactivated hypericin is even greater than that reported herein.

The data obtained from studies involving normal and malignant PBMC indicate that hypericin inhibits mitogen-induced proliferation of PBMC. Such inhibition is dependent on the concentration of hypericin and the duration of photoactivation. While not intending to be bound by any particular theory, it is understood that the inhibition of leukocyte proliferation which is exhibited by hypericin results from the capacity of hypericin to induce apoptotic cell death. This theory is supported by data obtained using a Terminal dUTP nick end labeling (TUNEL) assay of fragmented DNA obtained from either normal or malignant lymphocytes which were treated with hypericin.

The maximal proliferative level of PBMC in cultures which were illuminated for 20 minutes was observed to be lower than that in non-illuminated cultures. The patient having CTCL from whom the PBMC were obtained was, during the course of the experiments described in this example, being treated using extracorporeal photopheresis and may have had 8-methoxypsoralen (8-MOP) persisting in the blood. Residual 8-MOP may have contributed to the decreased maximal proliferative level following exposure to light.

In order to determine if residual 8-MOP was a contributing factor to the observed inhibition of leukocyte proliferation by hypericin, the following experiment was performed. PBMC from a patient to whom 8-MOP had been administered were illuminated for 20 minutes using the bank of visible fluorescent lights used in the experiments described in this example. Proliferation of these cells in response to ConA was measured. No illumination-dependent inhibition of proliferation of the leukocytes obtained from the patient who had been given 8-MOP was observed using visible light. This result suggests that illumination of 8-MOP-treated cells with visible light did not significantly affect their proliferative response.

Transformed Leukocytes

The results from studies involving leukocytes which were transformed using EBV are depicted in FIG. 3. In cultures of transformed leukocytes which were illuminated for 10 minutes, the $IC_{50}$ for hypericin was 3.2 µM. In cultures of transformed leukocytes which were illuminated for 30 minutes, the $IC_{50}$ for hypericin was 0.75 µM, and complete inhibition of cell proliferation was observed at a concentration of 3.2 µM hypericin. In contrast, in cultures of transformed leukocytes which were not illuminated, the $IC_{50}$ for hypericin was 36 µM. In contrast to the results obtained using normal leukocytes, illumination of transformed leukocytes for a period of 30 minutes resulted in inhibition of leukocyte proliferation that was greater than that which resulted from illumination for a period of 10 or 20 minutes. These results indicate that the optimal period of photoactivation of hypericin may be expected to vary, depending upon the characteristics of the leukocytes to be affected. One of skill in the art is able to determine the optimal period of photoactivation by performing experiments analogous to those described in this example, using a leukocyte type of interest, and by simply varying the period of illumination.

Photoactivation of Hypericin Using Ultraviolet-A Light

As indicated in FIG. 4, hypericin exhibits absorbance in the UV-A region of the electromagnetic spectrum. The ability of hypericin to inhibit proliferation of leukocytes upon illumination using UV-A light was therefore compared with the ability of another known photosensitizer, 8-MOP, to inhibit proliferation of leukocytes upon illumination using UV-A light.

The ability of 8-MOP to inhibit proliferation of EBV-transformed leukocytes was not enhanced upon illumination using visible light, as indicated by the data depicted in FIG. 5. In the absence of visible light illumination, the $IC_{50}$ for 8-MOP was 19.4 µM; following 30 minutes of visible light illumination, the $IC_{50}$ for 8-MOP was 18.9 µM. In contrast, as indicated by the data depicted in FIG. 3, the ability of hypericin to inhibit proliferation of EBV-transformed leukocytes was enhanced significantly upon illumination using visible light. In the absence of visible light illumination, the $IC_{50}$ for hypericin was 36 µM; following 30 minutes of visible light illumination, the $IC_{50}$ for hypericin was 0.75 µM.

The ability of both 8-MOP and hypericin to inhibit proliferation of EBV-transformed leukocytes was enhanced significantly upon illumination using UV-A light. In the absence of UV-A illumination, the $IC_{50}$ for 8-MOP was 19.4 µM and the $IC_{50}$ for hypericin was 36 µM; following application of 2 $J/cm^2$ UV-A illumination, the $IC_{50}$ for 8-MOP was 0.7 µM and the $IC_{50}$ for hypericin was 2.0 µM.

Furthermore, the ability of hypericin to inhibit cell proliferation was essentially the same whether 2 J/cm2 or 1 J/cm2 of UV-A illumination was applied. In contrast, the ability of 8-MOP to inhibit cell proliferation roughly doubled when 2 $J/cm^2$ of UV-A illumination was applied, relative to when 1 $J/cm^2$ of UV-A illumination was applied. These results indicate that maximal photoactivation of hypericin requires less UV-A illumination than is necessary to maximally photoactivate 8-MOP. Hence, the use of hypericin permits minimization of exposure of a patient to UV illumination and, therefore, minimization of the undesirable effects of UV illumination in the patient.

The methods described in this example may also be used to predict the in vivo response of normal, malignant, or transformed leukocytes in a mammal to administration to the mammal of an appropriate hypericin derivative.

EXAMPLE 2

Induction of Apoptosis of Neoplastic Leukocytes using Photoactivated Hypericin

The ability of photoactivated hypericin to induce apoptosis in PBMC obtained from a patient having CTCL was investigated. The ability of photoactivated hypericin to induce apoptosis in neoplastic leukocytes was also compared with the ability of photoactivated 8-MOP to induce apoptosis in neoplastic leukocytes. The processing of neoplastic leukocytes, the media and stock solutions used, and the procedures which were used were the same as those presented in Example 1, except as described below.

Neoplastic leukocytes were incubated in the presence of 10 µM hypericin or 100 ng/ml 8-MOP. Cultures were illuminated using fluorescent light for 20 minutes, illuminated with 2 $J/cm^2$ UV-A light or were not illuminated. After 24 and 48 hours, apoptosis was measured using a TUNEL assay, as described (Sgonc, 1994 Trends Gen. 10:41–42). The TUNEL assay specifically labels free ends of internucleosomally-cleaved DNA—the hallmark of the apoptotic process. A summary of the results of these experiments is presented in Table 2.

TABLE 2

Induction of apoptosis of PBMC obtained from a patient having CTCL following incubation of the PBMC with hypericin, with 8-MOP, or with neither ("control"). Numerical values represent the percentage of PBMC which underwent apoptosis, as assessed by TUNEL assay. Delay refers to the elapsed interval between the beginning of illumination and measurement of apoptosis. "ND" means not determined.

| Treatment | Delay (hours) | Type of Light | | |
|---|---|---|---|---|
| | | None | Visible | UV-A |
| Control | 24 | 8 | 10.3 | 23.3 |
| | 48 | 16.5 | ND | ND |
| 10 µM Hypericin | 24 | 11.5 | 97 | 88 |
| | 48 | 18 | 91 | 96 |
| 100 ng/ml 8-MOP | 24 | 11.5 | 32 | 87 |
| | 48 | 21 | 48 | 94 |

The results depicted in Table 2 indicate that hypericin is a much more potent inducer of apoptosis of malignant leukocytes than 8-MOP, when visible light is used for photoactivation. The results further indicate that hypericin and 8-MOP are approximately equally potent inducers of apoptosis of malignant leukocytes, when UV-A light is used for photoactivation.

The results of the experiments described in this example are supported by the results of flow cytometric sorting of malignant leukocytes which were treated with 10 μM hypericin or with 0.462 μM 8-MOP, or which were untreated. Hypericin-treated malignant leukocytes and 8-MOP-treated leukocytes were photoactivated using visible light for 20 minutes or 2 J/cm² UV-A light, or were not photoactivated, as described in Example 1. 18 hours after photoactivation, or 18 hours after preparation of the cultures which were not photoactivated, leukocyte cultures were harvested, and apoptotic cells were separated from non-apoptotic cells using a FACScan flow cytometer (Becton Dickinson Immunocytometry Systems, San Jose, Calif.). Apoptotic cells were distinguished from non-apoptotic cells based on increased dUTP-FITC incorporation.

The results of the sorting of cells from these cultures are depicted in FIG. 8. As shown in FIG. 8, Panels B and E, neither hypericin nor 8-MOP induced significant apoptosis in the absence of photoactivation. As shown in FIG. 8, Panels C and F, visible-light-activated hypericin induced apoptosis in nearly all cells, while visible-light-activated 8-MOP induced apoptosis in only a limited number of cells. In addition, in FIG. 8, Panels D and G, it is evident that both UV-A-activated hypericin and UV-A-activated 8-MOP induced apoptosis in most cells.

The results of the experiments described in this example demonstrate that hypericin is useful for inducing apoptosis in malignant leukocytes. The methods described in this example may also be used to predict the in vivo apoptotic response of malignant leukocytes in a mammal to administration to the mammal of an appropriate hypericin derivative.

EXAMPLE 3

Induction of Apoptosis in PBMC by UV- and Visible-Light-Activated Hypericin

The experiments described in this example demonstrate that hypericin activated by either visible or UV-A light induces apoptosis of malignant leukocytes.

The processing of neoplastic leukocytes, the media and stock solutions used, and the procedures which were used were the same as those presented in Example 1. Normal and malignant leukocytes were cultured, as described, in the presence of 1 μM hypericin, 10 μM hypericin, 1 μM 8-MOP, or 10 μM 8-MOP, and were exposed to fluorescent visible light for twenty minutes, to 2 J/cm² UV-A light, or were not exposed to a light source. The percentage of cells which underwent apoptosis was assessed by TUNEL assay performed 18 hours after illumination, or 18 hours after preparation of cultures which were not exposed to a light source.

The results of the experiments described in this example are presented in Table 3.

TABLE 3

Induction of apoptosis in PBMC obtained from a normal human subject ("Normal") or from a subject having CTCL ("CTCL") by hypericin or 8-MOP following activation with visible or ultraviolet light. Numerical values represent the percentage of PBMC which underwent apoptosis. "Medium" refers to a culture in which culture medium was added in place of either hypericin or 8-MOP. "Vehicle" refers to a culture to which an amount of benzyl alcohol in medium was added, which amount was equivalent to the amount of benzyl alcohol that was present in the hypericin-treated cultures.

| | Type of Light | | | | | |
|---|---|---|---|---|---|---|
| | None | | Visible | | UV-A | |
| Cell Type | Normal | CTCL | Normal | CTCL | Normal | CTCL |
| Medium | 4.6 | 2.3 | 13.7 | 9.9 | 22.1 | 27.3 |
| Vehicle | 7.1 | 2.1 | 10.6 | 10.3 | 16.3 | 23.3 |
| 1 μM Hypencin | 4.8 | 2.6 | 18.2 | 17.2 | 21.2 | 26.1 |
| 10 μM Hypericin | 5.4 | 2.8 | 87.9 | 94.3 | 37.3 | 94.4 |
| 1 μM 8-MOP | 3.8 | 2.5 | 13.7 | 11.0 | 22.9 | 44.0 |
| 10 μM 8-MOP | 6.8 | 2.4 | 15.3 | 12.2 | 63.0 | 74.3 |

The data shown in Table 3 indicate that hypericin, but not 8-MOP, is capable of inducing apoptosis in both normal and malignant leukocytes following illumination with visible light. The data also indicate that both hypericin and 8-MOP are capable of inducing apoptosis in malignant leukocytes following illumination with UV-A light. Surprisingly, the capacity of UV-A-activated hypericin to induce apoptosis of malignant leukocytes was significantly greater than its capacity to induce apoptosis of normal leukocytes. Although UV-A-activated 8-MOP also selectively induced apoptosis of malignant leukocytes, relative to normal leukocytes, the magnitude of the selective effect was much smaller.

The results of the experiments described in this example indicate that hypericin activated using UV-A or visible light is useful for inducing apoptosis of malignant leukocytes. This result directly contradicts the teaching in the prior art (Jarvis, et al., Canc. Res. 54:1707–1714), which indicates that hypericin is not useful for inducing apoptosis in malignant leukemia cells. These findings establish that photoactivated hypericin is useful for removing malignant leukocytes from a population of normal leukocytes. Visible light- or UV-A-activated hypericin is therefore useful for the treatment of leukocyte-associated diseases, such as leukemia, lymphoma, psoriasis, etc. The methods described in this example may also be used to predict the in vivo apoptotic response of normal and malignant leukocytes in a mammal to administration to the mammal of an appropriate hypericin derivative.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting proliferation of a leukocyte of a mammal, comprising administering an appropriate hypericin derivative to a population of mammalian leukocytes and photoactivating the appropriate hypericin derivative, thereby inhibiting proliferation of the leukocyte.

2. The method of claim 1, wherein proliferation of a leukocyte is characterized by accumulation of the leukocyte.

3. A method of inducing apoptosis in a leukocyte of a mammal, comprising administering an appropriate hypericin derivative to a population of mammalian leukocytes and photoactivating the appropriate hypericin derivative, thereby inducing apoptosis in the leukocyte.

4. The method of claim 3, wherein the appropriate hypericin derivative is selected from the group which consists of hypericin, protohypericin, and pseudohypericin.

5. The method of claim 3, wherein the step of photoactivating the appropriate hypericin derivative comprises providing illumination from a visible light source.

6. The method of claim 5, wherein the visible light source emits light having a wavelength between about 500 nm and about 650 nm.

7. The method of claim 3, wherein the step of photoactivating the appropriate hypericin derivative comprises providing illumination from a UV-A light source.

8. The method of claim 3, wherein the leukocyte is contained within a tissue of the mammal, and wherein the appropriate hypericin derivative is administered in a composition comprising a pharmaceutically acceptable carrier.

9. The method of claim 8, wherein the tissue is a dermatological tissue.

10. The method of claim 9, wherein photoactivation of the appropriate hypericin derivative is performed after administering the composition.

11. The method of claim 10, wherein administering the composition comprises topically administering the composition to the mammal.

12. The method of claim 11, wherein photoactivating the appropriate hypericin derivative comprises illuminating the dermatological tissue of the mammal.

13. The method of claim 10, wherein administering the composition comprises orally administering the composition to the mammal.

14. The method of claim 13, wherein photoactivating the appropriate hypericin derivative comprises illuminating the dermatological tissue of the mammal.

15. The method of claim 8, wherein the tissue is a blood tissue.

16. The method of claim 15, wherein photoactivation of the appropriate hypericin derivative is performed after administering the composition.

17. The method of claim 16, wherein administering the composition comprises topically administering the composition to the mammal.

18. The method of claim 17, wherein photoactivating the appropriate hypericin derivative comprises illuminating a dermatological tissue of the mammal.

19. The method of claim 17, wherein photoactivating the appropriate hypericin derivative comprises extracorporeally illuminating the blood tissue of the mammal.

20. The method of claim 16, wherein administering the composition comprises orally administering the composition to the mammal.

21. The method of claim 20, wherein photoactivating the appropriate hypericin derivative comprises illuminating a dermatological tissue of the mammal.

22. The method of claim 20, wherein photoactivating the appropriate hypericin derivative comprises extracorporeally illuminating the blood tissue of the mammal.

23. The method of claim 8, wherein the mammal is afflicted with a hypericin-sensitive disease.

24. The method of claim 23, wherein the hypericin-sensitive disease is selected from the group consisting of a leukocyte-associated disease, cutaneous T-cell lymphoma, myeloma, mastocytosis, an eosinophilic condition, transplant rejection, graft-versus-host disease, an EBV-mediated lymphoma, Burkitt's lymphoma, infectious mononucleosis, an EBV-associated B-cell lymphoma, an EBV-associated mesenchyal cutaneous tumor, a systemic immunologic process, an autoimmune disease, leukemia, lymphoma, psoriasis, a polymorphonuclear cell-related disease, Sweet's disease, pyoderma gangrenosum, and an allergic reaction.

25. The method of claim 24, wherein the mammal is a human, wherein the hypericin-sensitive disease is psoriasis, wherein the dermatological tissue of the human is a psoriatic tissue, and wherein illuminating the psoriatic tissue comprises exposing the psoriatic tissue to a visible light source.

26. The method of claim 24, wherein the mammal is a human, wherein the hypericin-sensitive disease is cutaneous T-cell lymphoma, and wherein illuminating the dermatological tissue comprises exposing the dermatological tissue to a UV-A light source.

27. The method of claim 3, wherein photoactivating the appropriate hypericin derivative is continued until apoptosis has been induced in substantially all leukocytes in the mammal.

28. The method of claim 27, wherein the mammal is a human.

29. The method of claim 28, wherein the human is a human in need of a bone marrow transplant.

30. The method of claim 28, wherein the human is afflicted with leukemia.

\* \* \* \* \*